US011815435B2

(12) United States Patent
Bose et al.

(10) Patent No.: US 11,815,435 B2
(45) Date of Patent: Nov. 14, 2023

(54) BETA GLUCAN IMMUNOPHARMACODYNAMICS

(71) Applicant: HiberCell, Inc., New York, NY (US)

(72) Inventors: Nandita Bose, Plymouth, MN (US); Nadine Ottoson, Lakeville, MN (US); Ben Harrison, Eagan, MN (US); Jamie Lowe, Woodbury, MN (US); Mark Uhlik, Indianapolis, IN (US); Jeremy Graff, Indianapolis, IN (US); Richard Huhn, St. Paul, MN (US)

(73) Assignee: HiberCell, Inc., New York, NY (US)

( * ) Notice: Subject to any disclaimer, the term of this patent is extended or adjusted under 35 U.S.C. 154(b) by 722 days.

(21) Appl. No.: 16/488,911

(22) PCT Filed: Feb. 23, 2018

(86) PCT No.: PCT/US2018/019412
§ 371 (c)(1),
(2) Date: Aug. 26, 2019

(87) PCT Pub. No.: WO2018/156888
PCT Pub. Date: Aug. 30, 2018

(65) Prior Publication Data
US 2020/0033362 A1 Jan. 30, 2020

Related U.S. Application Data

(60) Provisional application No. 62/578,091, filed on Oct. 27, 2017, provisional application No. 62/463,332, filed on Feb. 24, 2017.

(51) Int. Cl.
G01N 33/68 (2006.01)
A61K 31/716 (2006.01)

(52) U.S. Cl.
CPC ....... G01N 33/6854 (2013.01); A61K 31/716 (2013.01); G01N 2400/24 (2013.01); G01N 2800/52 (2013.01)

(58) Field of Classification Search
CPC .......... G01N 33/6854; G01N 2400/24; G01N 2800/52; A61K 31/716
USPC ....................................................... 514/54
See application file for complete search history.

(56) References Cited

U.S. PATENT DOCUMENTS

| 4,810,646 A | 3/1989 | Jamas et al. |
| 4,962,094 A | 10/1990 | Jamas et al. |
| 5,028,703 A | 7/1991 | Jamas et al. |
| 5,032,401 A | 7/1991 | Jamas et al. |
| 5,082,936 A | 1/1992 | Jamas et al. |
| 5,214,337 A | 5/1993 | Ishibashi |
| 5,250,436 A | 10/1993 | Jamas et al. |
| 5,322,841 A | 6/1994 | Jamas et al. |
| 5,397,773 A | 3/1995 | Donzis |
| 5,488,040 A | 1/1996 | Jamas et al. |
| 5,504,079 A | 4/1996 | Jamas et al. |
| 5,506,124 A | 4/1996 | Jamas et al. |
| 5,519,009 A | 5/1996 | Donzis |
| 5,532,223 A | 7/1996 | Jamas et al. |
| 5,576,015 A | 11/1996 | Donzis |
| 5,607,677 A | 3/1997 | Jamas et al. |
| 5,622,939 A | 4/1997 | Jamas et al. |
| 5,622,940 A | 4/1997 | Ostroff |
| 5,633,369 A | 5/1997 | Jamas et al. |
| 5,663,324 A | 9/1997 | Jamas et al. |
| 5,702,719 A | 12/1997 | Donzis |
| 5,705,184 A | 1/1998 | Donzis |
| 5,741,495 A | 4/1998 | Jamas et al. |
| 5,783,569 A | 7/1998 | Jamas et al. |
| 5,811,542 A | 9/1998 | Jamas et al. |
| 5,817,643 A | 10/1998 | Jamas et al. |
| 5,849,720 A | 12/1998 | Jamas et al. |
| 6,020,324 A | 2/2000 | Jamas et al. |
| 6,046,323 A | 4/2000 | Park |

(Continued)

FOREIGN PATENT DOCUMENTS

| AU | 2013-203785 A1 | 5/2013 |
| CN | 101553261 A | 10/2009 |

(Continued)

OTHER PUBLICATIONS

Antonysamy et al. Endogenous anti-β-glucan antibodies, a potential predictive biomarker for the efficacy of soluble yeast β-1,3/1,6 glucan (Imprime PGG®) immunotherapy in cancer patients (VAC3P. 947). J Immunol 192(sup 1):73.9 (Abstract) (2014).

Bacon et al. The glucan components of the cell wall of baker's yeast (Saccharomyces cerevisiae) considered in relation to its ultrastructure. Biochem J 114(3):557-567 (1969).

Barbee et al. Current Status and Future Directions of the Immune Checkpoint Inhibitors Ipilimumab, Pembrolizumab, and Nivolumab in Oncology. Ann Pharmacother 49(8):907-937 (2015).

(Continued)

Primary Examiner — Yih-Horng Shiao
(74) Attorney, Agent, or Firm — Goodwin Procter LLP

(57) ABSTRACT

This disclosure provides, in one aspect, dosing strategies for soluble β-glucan immunotherapy to optimize acute immunopharmacodynamic responses for the immunotherapy and/or subject. It also provides a method for analyzing a sample from a subject for a biomarker to identify the appropriate dosing strategy for soluble β-glucan immunotherapy. Generally, the method includes obtaining a biological sample from a subject, analyzing the sample for a biomarker anti-β-glucan antibody level or immunopharmacodynamic response level, classifying the subject into a subgroup based on the biomarker anti-β-glucan antibody level or immunopharmacodynamic response level and identifying the appropriate dosing strategy based on the subgroup classification.

7 Claims, 45 Drawing Sheets

(56) References Cited

U.S. PATENT DOCUMENTS

| | | |
|---|---|---|
| 6,084,092 A | 7/2000 | Wakshull et al. |
| 6,090,938 A | 7/2000 | Wakshull et al. |
| 6,110,692 A | 8/2000 | Wakshull et al. |
| 6,117,850 A | 9/2000 | Patchen et al. |
| 6,143,731 A | 11/2000 | Jamas et al. |
| 6,143,883 A | 11/2000 | Lehmann et al. |
| 6,242,594 B1 | 6/2001 | Kelly |
| 6,294,321 B1 | 9/2001 | Wakshull et al. |
| 6,355,625 B1 | 3/2002 | Pavliak et al. |
| 6,369,216 B1 | 4/2002 | Patchen et al. |
| 6,413,715 B2 | 7/2002 | Wakshull et al. |
| 6,630,310 B1 | 10/2003 | Wakshull et al. |
| 7,022,685 B2 | 4/2006 | Patchen et al. |
| 7,981,447 B2 | 7/2011 | Cox |
| 8,617,823 B2 | 12/2013 | Rubin-Bejerano et al. |
| 9,885,726 B2 * | 2/2018 | Bose .................. A61P 37/02 |
| 9,943,607 B2 | 4/2018 | Bose et al. |
| 10,092,646 B2 | 10/2018 | Grossman et al. |
| 10,111,900 B2 | 10/2018 | Bose et al. |
| 10,111,901 B2 | 10/2018 | Bose et al. |
| 10,114,027 B2 * | 10/2018 | Bose ................ G01N 33/56961 |
| 11,229,701 B2 | 1/2022 | Grossman et al. |
| 2002/0032170 A1 | 3/2002 | Jamas et al. |
| 2004/0014715 A1 | 1/2004 | Ostroff |
| 2004/0082539 A1 | 4/2004 | Kelly |
| 2004/0116380 A1 | 6/2004 | Jamas et al. |
| 2005/0245480 A1 | 11/2005 | Ostroff et al. |
| 2006/0009419 A1 | 1/2006 | Ross et al. |
| 2006/0165700 A1 | 7/2006 | Ostroff et al. |
| 2006/0247205 A1 | 11/2006 | Patchen et al. |
| 2007/0042930 A1 | 2/2007 | Ross et al. |
| 2007/0059310 A1 | 3/2007 | Karel |
| 2008/0063650 A1 | 3/2008 | Yan |
| 2008/0103112 A1 | 5/2008 | Magee et al. |
| 2008/0108114 A1 | 5/2008 | Cox et al. |
| 2008/0167268 A1 | 7/2008 | Yan |
| 2009/0047288 A1 | 2/2009 | Yan |
| 2009/0074761 A1 | 3/2009 | Yan |
| 2009/0163439 A1 | 6/2009 | Ostroff et al. |
| 2009/0169557 A1 | 7/2009 | Ross et al. |
| 2010/0297130 A1 | 11/2010 | Cassone et al. |
| 2010/0330597 A1 | 12/2010 | Tsuchiya |
| 2011/0112048 A1 | 5/2011 | Cox et al. |
| 2011/0183353 A1 | 7/2011 | Poulain |
| 2012/0045779 A1 | 2/2012 | Abe et al. |
| 2014/0105935 A1 | 4/2014 | Bose et al. |
| 2014/0314804 A1 | 10/2014 | Gorden et al. |
| 2014/0314834 A1 | 10/2014 | Paya Cuenca et al. |
| 2015/0125451 A1 | 5/2015 | Grossman et al. |
| 2015/0125461 A1 | 5/2015 | Grossman et al. |
| 2015/0273033 A1 | 10/2015 | Bosch et al. |
| 2016/0305955 A1 | 10/2016 | Bose et al. |
| 2017/0027210 A1 | 2/2017 | Cox et al. |
| 2019/0022129 A1 | 1/2019 | Bose et al. |
| 2019/0060350 A1 | 2/2019 | Bose et al. |
| 2019/0060351 A1 | 2/2019 | Bose et al. |
| 2021/0121527 A1 | 4/2021 | Aguirre-Ghiso |
| 2021/0283168 A1 | 9/2021 | Bose et al. |
| 2022/0105181 A1 | 4/2022 | Grossman et al. |

FOREIGN PATENT DOCUMENTS

| | | |
|---|---|---|
| CN | 103796680 A | 5/2014 |
| EP | 2032180 A2 | 3/2009 |
| HK | 1138215 A1 | 10/2014 |
| JP | H05503952 A | 6/1993 |
| JP | H06107702 A | 4/1994 |
| JP | 2001342257 A | 12/2001 |
| JP | 2002105101 A | 4/2002 |
| JP | 2006502167 A | 1/2006 |
| JP | 2006507239 A | 3/2006 |
| JP | 2007-155334 A | 6/2007 |
| JP | 2007-205842 A | 8/2007 |
| JP | 2007531700 A | 11/2007 |
| JP | 2008500623 A | 1/2008 |
| JP | 2008-164579 A | 7/2008 |
| JP | 2009515512 A | 4/2009 |
| JP | 2009528267 A | 8/2009 |
| JP | 2009540106 A | 11/2009 |
| JP | 2010-237126 A | 10/2010 |
| JP | 2011501691 A | 1/2011 |
| JP | 2014025079 A | 2/2014 |
| SG | 164426 | 9/2010 |
| WO | WO-9103495 A1 | 3/1991 |
| WO | WO-9404163 A1 | 3/1994 |
| WO | WO-03070234 A1 | 8/2003 |
| WO | WO-2003/097091 A2 | 11/2003 |
| WO | WO-2004014320 A2 | 2/2004 |
| WO | WO-2004033502 A1 | 4/2004 |
| WO | WO-2005120251 A1 | 12/2005 |
| WO | WO-2006121168 A1 | 11/2006 |
| WO | WO-2007/084661 A2 | 7/2007 |
| WO | WO-2007146416 A2 | 12/2007 |
| WO | WO-2009014708 A2 | 1/2009 |
| WO | WO-2009/134891 A2 | 11/2009 |
| WO | WO-2012/154680 A2 | 11/2012 |
| WO | WO-2012154680 A2 | 11/2012 |
| WO | WO-2012154818 A1 | 11/2012 |
| WO | WO-2012167061 A1 | 12/2012 |
| WO | WO-2012177624 A3 | 4/2013 |
| WO | WO-2013079174 A1 | 6/2013 |
| WO | WO-2013165591 A1 | 11/2013 |
| WO | WO-2013165593 A1 | 11/2013 |
| WO | WO-2014127917 A1 | 8/2014 |
| WO | WO 2015/084732 * | 6/2015 |
| WO | WO-2015095811 A2 | 6/2015 |
| WO | WO-2016007876 A1 | 1/2016 |
| WO | WO-2016073763 A2 | 5/2016 |
| WO | WO-2017120604 A1 | 7/2017 |
| WO | WO-2018156888 A1 | 8/2018 |

OTHER PUBLICATIONS

Barker et al. Pharmacokinetic/pharmacodynamic modelling approaches in paediatric infectious diseases and immunology. Adv Drug Deliv Rev 73:127-39 (2014).

Belen et al. Safety and Efficacy of Imprime PGG Plus Cetuximab, with Irinotecan and without Irinotecan, in Patients with Advanced Colorectal Cancer: A Phase 1b/2 Study with KRAS Subpopulation Analysis. ESMO Poster (1 pg.) (2010).

Belen et al. Safety, Pharmacokinetics, and Efficacy of Imprime PGG Plus Cetuximab, with and without Irinotecan, in Advanced Metastatic Colorectal Cancer Patients. EMSO Poster CRC0713 (1 pg.) (2010).

Bell et al. The structure of a cell-wall polysaccharide of Baker's yeast. J Chem Soc, pp. 1944-1947 (1950).

Berenbaum et al. Synergy, additivism and antagonism in immunosuppression. Clin Exp Immunol 28:1-18 (1977).

Biothera—Efficacy/Safety of Imprime PGG Injection With Bevacizumab and Paclitaxel/Carboplatin in Patients With Untreated Advanced Non-Small Cell Lung Cancer. Clinicaltrials.gov (https://clinicaltrials.gov/ct2/show/NCT00874107) (20 pgs.) (May 5, 2015).

Blagovic et al. Lipid composition of brewer's yeast. Food Technol. Biotechnol. 39:175-181 (2001).

Bose et al. Activation of the Classical Complement Pathway is Required For Cancer Immunotherapy Efficacy Involving the Combination of an Anti-Tumor Monoclonal Antibody and Soluble Yeast β-1,3/1,6 Glucan (Imprime PGG®) (Abstract/program # J4). Keystone Symposium, Vancouver, BC, Canada, Jan. 2013 (1 pg).

Bose et al. Binding of Soluble Yeast β-Glucan to Human Neutrophils and Monocytes is Complement-Dependent. Front Immunol 4:230 (2013).

Bristol Myers Squibb—Study of Nivolumab (BMS-936558) in Combination With Gemcitabine/Cisplatin, Pemetrexed/Cisplatin, Carboplatin/Paclitaxel, Bevacizumab Maintenance, Erlotinib, Ipilimumab or as Monotherapy in Subjects With Stage 111B/IV Non-small Cell Lung Cancer (NSCLC). Clinicaltrials.gov (https://clinicaltrials.gov/archive/NCT01454102/2015_11_19). (31 pgs.) (May 19, 2015).

(56) References Cited

OTHER PUBLICATIONS

Callahan et al. Phase I/II, open-label study of nivolumab (anti-PD-1; BMS-936558, ONO-4538) as monotherapy or combined with ipilimumab in advanced or metastatic solid tumors. J Clin Oncol 32:15 (Suppl TPS3114) (2 pgs) (2014).
Chan et al. The effects of β-glucan on human immune and cancer cells. J Hematol Oncol 2:25 (11 pgs) (2009).
Chiba et al. Recognition of tumor cells by Dectin-1 orchestrates innate immune cells for anti-tumor responses. Elife 3:e04177 (2014).
Chou. Drug Combination Studies and Their Synergy Quantification Using the Chou-Talalay Method. Cancer Res 70(2):440-446 (2010).
Daou et al. Oat Beta-Glucan: Its Role in Health Promotion and Prevention of Diseases. Comprehensive Reviews in Food Science and Food Safety 11:355-365 (2012).
Deman. Chapter 2. Lipids In Principles of Food Chemistry© 1985. AVI Publishing Co., Inc. (57 pgs.).
Engel-Riedel et al. Imprime PGG, a Novel Innate Immune Modulator, in the 1St-Line Treatment of Stage IV NSCLC: Results From a Randomized, Controlled, Multicenter Phase 2 Study. European Society of Medical Oncology Congress 2014, Madrid, Spain. Oral Poster Session. Sep. 2014 (1 pg.).
Gowrishankar et al. Inducible but Not Constitutive Expression of PD-L1 in Human Melanoma Cells is Dependent on Activation of NF-KB. PLoS One (pp. 1-19) (2015).
Gumbo et al. Pharmacokinetic-Pharmacodynamic and Dose-Response Relationships of Antituberculosis Drugs: Recommendations and Standards for Industry and Academia. J Infect Dis. 211 (Suppl 3):S96-S106 (2015).
Hamid et al. Safety and tumor responses with lambrolizumab (anti-PD-1) in melanoma. N Eng J Med. 369:134-144 (2013).
Hassad et al. The Molecular Constitution of an Insoluble Polysaccharide from Yeast, *Saccharomyces cerevisiae*. Contribution from the Divisions of Plant Nutrition and Fruit Products, College of Agriculture, University of California, pp. 295-298 (1941).
Hunter et al. Preparation of microparticulate beta-glucan from *Saccharomyces cerevisiae* for use in immune potentiation. Lett Appl Microbiol 35(4):267-271 (2002).
Ishibashi et al. Analysis of the titer and reactivity of antibody/ies against fungal cell wall β-glucans in human sera. Journal of Medicinal Mushrooms 15:115-126 (2013).
Jonas et al. Imprime PGG, a yeast β-glucan immunomodulator, can engage Fc gamma receptor (FcγR) in addition to complement receptor 3 (CR3) on human neutrophils and monocytes. (Abstract # 2019/ program # J7). Keystone Symposium, Banff, Alberta, Canada, Feb. 2015 (1 pg.).
Li et al. Combined yeast beta-glucan and antitumor monoclonal antibody therapy requires C5a-mediated neutrophil chemotaxis via regulation of decay-accelerating factor CD55. Cancer Res 67(15):7421-7430 (2007).
Li et al. Yeast beta-glucan amplifies phagocyte killing of iC3b-opsonized tumor cells via complement receptor 3-Syk-phosphatidylinositol 3-kinase pathway. J Immunol 177(3):1661-1669 (2006).
Manners et al. The structure of a β-(1→>6)-d-glucan from yeast cell walls. Biochemical Journal 135:19-30 (1973).
Misaki et al. Structure of the cell-wall glucan of yeast (*Saccharomyces cerevisiae*). Carbohydrate Research 6(2):150-164 (1968).
Modak et al. Rituximab therapy of lymphoma is enhanced by orally administered (1→3),(1→4)-D-beta-glucan. Leuk Res 29(6):679-683 (2005).
Nawar. Chapter 4. Lipids in Food Chemistry. © 1985. Editor: Owen R. Fennema. Marcel Dekker, Inc. (110 pgs).
Nelson. FDA Approves Ramucirumab for Non-small Cell Lung Cancer. Medspace (http://www.medscape.com/viewarticle/836523) (7 pgs.) (Dec. 12, 2014).
Obeid et al. The role of tumor-associated macrophages in breast cancer progression. Int J Oncol 43:5-12 (2013).
Patchen et al. A Phase 3 Open-Label, Randomized, Multicenter Study of Imprime PGG in Combination With Cetuximab in Patients With KRAS Wild Type Metastatic Colorectal Cancer. European Society of Medical Oncology Congress 2014, Madrid, Spain. Sep. 2014 (1 pg.).
PCT/US2015/039977 International Search Report and Written Opinion dated Oct. 13, 2015.
PCT/US2015/059304 International Search Report and Written Opinion dated Jun. 30, 2016.
PCT/US2017/012766 International Preliminary Report on Patentability dated Jul. 19, 2018.
PCT/US2017/012766 International Search Report and Written Opinion dated Mar. 31, 2017.
PCT/US2018/019412 International Search Report and Written Opinion dated Jul. 10, 2018.
Philips et al. Therapeutic uses of anti-PD-1 and alai-PD-L1 antibodies. Int Immunol 27(1):39-46 (2014).
Qi et al. Differential pathways regulating innate and adaptive antitumor immune responses by particulate and soluble yeast-derived β-glucans. Blood 117(25):6825-6836 (2011).
Qui et al. Serum Levels of Natural Anti- β-Glucan Antibodies Correlate to Binding and Immunomodulatory Functions of Yeast-Derived β-Glucan: A Potential Predictive Biomarker in Cancer Immunotherapy? (Abstract #X1 1020/program #X1). Keystone Symposium, Whistler, BC, Canada, Mar. 2014 (1 pg.).
Salvador et al. Yeast-derived beta-glucan augments the therapeutic efficacy mediated by anti-vascular endothelial growth factor monoclonal antibody in human carcinoma xenograft models. Clin Cancer Res 14(4):1239-1247 (2008).
Sanford et al. Inflammatory Monocyte Mobilization Decreases Patient Survival in Pancreatic Cancer: A Role for Targeting the CCL2/CCR2 Axis. Clin Cancer Res 19(13):3404-15 (2013).
Schneller et al. Chemoimmunotherapy of Advanced Non-Small Cell Lung Cancer With Imprime PGG in Combination With Cetuximab, Carboplatin and Paclitaxel—Analysis of Secondary Endpoints of a Multicenter, Randomized Phase 2 Trial. European Society of Medical Oncology Congress 2014 Poster, Madrid, Spain. (1 pg.) (Sep. 2014).
Segal et al. Imprime PGG Plus Cetuximab Therapy For Advanced KRAS Mutant Colorectal Cancer. European Society of Medical Oncology, World Congress on Gastrointestinal Cancer, Annals of Oncology (1 pg) (2011).
Tamayo et al. Safety, pharmacokinetics (PK), and efficacy of Imprime PGG plus cetuximab (cetux) with and without irnotecan (irino) in advanced metastatic colorectal cancer (mCRC) patients. European Society of Medical Oncology, World Congress on Gastrointestinal Cancer. Abstract No. 4584, Jul. 2010.
Thomas et al. Circulating Immune Complex Levels are Associated with Disease Severity and Seasonality in Children with Malaria from Mali. Biomark Insights 7:81-6 (2012).
Thomas et al. Imprime PGG Improves the Efficacy of Carboplatin, Paclitaxel and Cetuximab Chemoimmunotherapy of Advanced Non-Small Cell Lung Cancer (NSCLC) American Association of Clinical Research/International Association for the Study of Lung Cancer. Joint Conference on the Molecular Origins of Lung Cancer, Jan. 2014 (1 pg.).
Topalian et al. Safety, Activity, and Immune Correlates of Anti-PD-1 Antibody in Cancer. N Engl J Med 366:2443-2454 (2012).
U.S. Appl. No. 60/975,734, filed Sep. 27, 2007.
U.S. Appl. No. 15/386,781 Office Action dated Aug. 25, 2017.
U.S. Appl. No. 15/386,781 Office Action dated Feb. 16, 2017.
U.S. Appl. No. 15/386,781 Office Action dated Jan. 16, 2018.
U.S. Appl. No. 15/386,887 Office Action dated Feb. 16, 2017.
U.S. Appl. No. 15/386,887 Office Action dated Jan. 16, 2018.
Van Der Rest et al. The plasma membrane of Saccharomyces cerevisiae: structure, function, and biogenesis. Microbiol Rev. 59(2):304-322 (1995).
Vasilakos. Abstract 5627: Antitumor 1-15 activity of soluble beta-1,3/1,6 glucans: Structure matters 1. Retrieved from the Internet: http://cancerres.aacrjournals.org/content/70/8Supplement/5627 on Dec. 4, 2017. Cancer Research (3 pgs.) (2010) .
Wiesenthal. Feedback on Timing of biopsy relative to timing of ongoing cancer chemotherapy and/or radiation therapy. Available at http://weisenthal.org/feedback.htm (5 pgs.) (2002).

(56) References Cited

OTHER PUBLICATIONS

Yasuda et al. Simultaneous blockade of programmed death 1 and vascular endothelial growth factor receptor 2 (VEGFR2) induces synergistic anti-tumour effect in vivo. Clin Exp Immunol 172(3):500-506 (2013).

Zent et al. Early Treatment of High Risk Chronic Lymphocytic Leukemia with Alemtuzumab, Rituximab, and PGG Beta Glucan: A Phase 1 Clinical Trial. American Society of Hematology Annual Meeting. Blood 120:1792 (2012).

Zent et al. Early treatment of high risk chronic lymphocytic leukemia with alemtuzumab, rituximab and poly-(1-6)-beta-glucotriosyl-(1-3)-beta-glucopyranose beta-glucan is well tolerated and achieves high complete remission rates. Leuk Lymphoma 56(8):2373-2378 (2015).

Zhong et al. Effect of yeast-derived beta-glucan in conjunction with bevacizumab for the treatment of human lung adenocarcinoma in subcutaneous and orthotopic xenograft models. J Immunother 32(7):703-712 (2009).

Antonysamy et al., "Differential Neutrophil Binding of Imprime PGG®, A β-1,3/1,6 Immunomodulatory Glucan," International Symposium the Neutrophil in Immunity, 2014, abstract (1 page).

Chiani et al., "Anti-β-glucan antibodies in healthy human subject," Vaccine, 2009, 513-519.

Fraser et al., "Test result variation and the quality of evidence-based clinical guidelines," Clinica Chimica Acta, 2004, 346, 19-24.

Goodridge et al., "Activation of the innate immune receptor Dectin-1 upon formation of a "phagocytic synapse"," Nature, 2011, 472(7344), 471-475.

Ishibashi et al., "Characterization of Blood β1,3-glucan and Anti-βglucan Antibody in Hemodialysis Patients Using Culinary-Medicinal Royal Sun Agarics, Agaricus brasiensis S. Wasser et al." 2011, 13(2), 101-107.

Ishibashi et al., "Effect of Oral Administration of Dried Royal Sun Agaricus, Agaricus brasiensis S. Wasser et al. (Agaricomycetidae), Fruit Bodies on Anti-β-Glucan Antibody Titers in Humans," International Journal of Medicinal Mushrooms, 2009, 11(s), 117-131.

Ishibashi et al., "Influence of Anti-β-Glucan Antibody on Fungal Cell Wall β-Glucan Bioactivity," Journal of Japanese Society for Bacteriology, 2009, 64(1), 168, p. 1-240 (4 pages).

Isoda et al., "Clinical Efficacy of Superfine Dispersed Lentinan (β-1,3-glucan) in Patients with Hepatocellular Carcinoma," Hepato-Gastroenterology, 2009, 56, 437-441.

Leonardi et al., "Determination of Anti-Beta Glucan Immunoglobulin G by Means of the Elisa Enzyme Linked Immunosorbent Assay Method," Bulletin de La Societe Francaise de Lycologie Medicale, 1984, 13(1), 177-182 (11 pages).

Noss et al., "IgG to Various Beta-Glucans in a Human Adult Population," Allergy and Immunology, 2012, 157, 98-108.

Oka et al., "In Vitro and In Vivo Analysis of Human Leukocyte Binding by the Antitumor Polysaccharide, Lentinan," Int. J. Immunopharmac., 1996, 18, 3, 211-216.

Rubin-Bejerano et al., "Phagocytosis by Human Neutrophils is Stimulated by a Unique Fungal Cell Wall Component," Cell Host Microbe, 2007, 2(1), 55-67 (20 pages).

Thornton et al., "Analysis of the Sugar Specificity and Molecular Location of the β-Glucan-Binding Lectin Site of Complement Receptor Type 3 (CD11b/CD18)," Journal of Immunology, 1996, 156(3), 1235-1246.

Vasilakos et al., "Human innate immune cells that engage soluble beta-1,3/1,6-glucans: Role for complement receptors (CR3, CD11b/CD18),"The Journal of Immunology, 184(1), abstract (3 pages), (year 2010).

Xia et al., "The β-Glucan-Binding Lectin Site of Mouse CR3 (CD11b/CD18) and Its Function in Generating a Primed State of the Receptor That Mediates Cytotoxic Activation in Response to the iC3b-Opsonized Target Cells," Journal of Immunology, 1999, 162(4), 2281-2290.

\* cited by examiner

Increase in percent of CD16+ Monocytes

BETA GLUCAN IMMUNOPHARMACODYNAMICS

CROSS-REFERENCE TO RELATED APPLICATION

This application is a U.S. national stage patent application under 35 U.S.C. § 371 of International Application No. PCT/US2018/019412, filed Feb. 23, 2018, which claims the benefit of, and priority to, U.S. Provisional Patent Application Serial Nos. 62/463,332, filed on Feb. 24, 2017, and 62/578,091, filed on Oct. 27, 2017, the contents of each of which are incorporated herein by reference.

SUMMARY

This disclosure provides, in one aspect, a method for determining an appropriate dose of soluble β-glucan for a subject undergoing soluble β-glucan immunotherapy. Generally, the method includes obtaining a biological sample from a subject, analyzing the sample for a biomarker anti-β-glucan antibody level, classifying the subject in one of two or more predetermined subgroups based on the subject's anti-β-glucan antibody level and identifying the appropriate dose of soluble β-glucan that corresponds to such subgroup.

In some embodiments, the biomarker anti-β-glucan antibody can be IgG. In such embodiments, the predetermined subgroups may include a low anti-β-glucan antibody level subgroup and a high anti-β-glucan antibody level subgroup or the predetermined subgroups may include a low anti-β-glucan antibody level subgroup, a mid anti-β-glucan antibody level subgroup and a high anti-β-glucan antibody level subgroup.

In some embodiments, subjects classified in a low anti-β-glucan antibody level subgroup may be administered one or more pre-doses of soluble β-glucan.

In some embodiments, subjects classified in a mid anti-β-glucan antibody level subgroup may be administered a dose of at least 4 mg/kg soluble β-glucan.

In some embodiments, subjects classified in a high anti-β-glucan antibody level subgroup may be administered a dose of about 2 mg/kg soluble β-glucan.

In some embodiments, the β-glucan is derived from yeast such as, for example, a β-1,3/1,6 glucan. In certain embodiments, the β-glucan can include β(1,6)-[poly-(1,3)-D-glucopyranosyl]-poly-β(1,3)-D-glucopyranose.

In some embodiments, a subject's sample may be analyzed for immunopharmacodynamic responses to identify appropriate dosing.

In another aspect, this disclosure provides dosing schedules and methods of determining dosing schedules of soluble β-glucan to a subject to enhance the efficacy of soluble β-glucan immunotherapy.

In some embodiments, dosing schedules are timed to regulate the number of and/or interval between acute immunopharmacodynamic responses to soluble β-glucan administration.

In some embodiments, soluble β-glucan is administered to a subject one time during a course of treatment.

In some embodiments, soluble β-glucan is administered to a subject every 2, 3, 4, 5, 6, 7, 8, 9, 10, 11 or 12 weeks during a course of treatment.

In some embodiments, soluble β-glucan is administered to a subject every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 or 84 days.

In some embodiments, immunopharmacodynamic responses and/or anti-β-glucan antibody levels of a subject are analyzed prior to a course of treatment to determine the length of interval needed to regulate the subject's acute immunopharmacodynamic responses during the course of treatment.

In some embodiments, the β-glucan is derived from yeast such as, for example, a β-1,3/1,6 glucan. In certain embodiments, the β-glucan can include β(1,6)-[poly-(1,3)-D-glucopyranosyl]-poly-β(1,3)-D-glucopyranose.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1A:
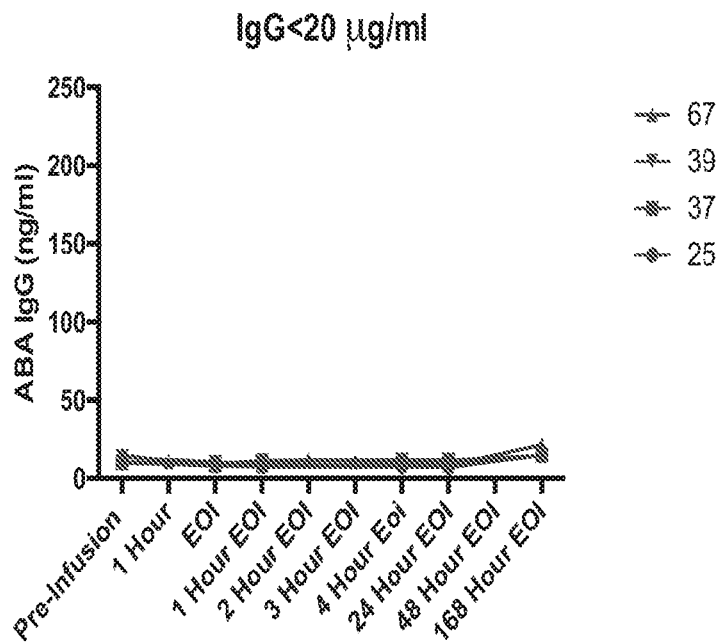
FIG. 1A. Anti-β-glucan antibody levels measured in serum of healthy human subjects classified as Low-ABA which were intravenously administered PGG.

β-glucans are polymers of glucose derived from a variety of microbiological and plant sources including, for example, yeast, bacteria, algae, seaweed, mushroom, oats, and barley. Of these, yeast β-glucans have been extensively evaluated for their immunomodulatory properties. Yeast β-glucans can be present as various forms such as, for example, intact yeast, zymosan, purified whole glucan particles, solubilized zymosan polysaccharide, or highly-purified soluble β-glucans of different molecular weights. Structurally, yeast β-glucans are composed of glucose monomers organized as a β-(1,3)-linked glucopyranose backbone with periodic β-(1, 3) glucopyranose branches linked to the backbone via β-(1, 6) glycosidic linkages. The different forms of yeast β-glucans can function differently from one another. The mechanism through which yeast β-glucans exert their immunomodulatory effects can be influenced by the structural differences between different forms of the β-glucans such as, for example, its particulate or soluble nature, tertiary conformation, length of the main chain, length of the side chain, and frequency of the side chains. The immune stimulating functions of yeast β-glucans are also dependent upon the receptors engaged in different cell types in different species, which again, can be dependent on the structural properties of the β-glucans.

In general, β-glucan immunotherapies can include administering to a subject any suitable form of β-glucan or any combination of two or more forms of β-glucan. Suitable β-glucans and the preparation of suitable β-glucans from their natural sources are described in, for example, U.S. Patent Application Publication No. US2008/0103112 A1. In some cases, the β-glucan may be derived from a yeast such as, for example, *Saccharomyces cerevisiae*. In certain cases, the β-glucan may be or be derived from β(1,6)-[poly-(1,3)-

D-glucopyranosyl]-poly-β(1,3)-D-glucopyranose, also referred to herein as PGG (IMPRIME PGG, Biothera, Eagan, Minn.), a highly purified and well characterized form of soluble yeast-derived β-glucan. Moreover, β-glucan-based immunotherapies can involve the use of, for example, a modified and/or derivatized β-glucan such as those described in International Patent Application No. PCT/US12/36795. In other cases, β-glucan immunotherapy can involve administering, for example, a particulate-soluble β-glucan or a particulate-soluble β-glucan preparation, each of which is described in, for example, U.S. Pat. No. 7,981,447.

weeks, then given a 2 week wash out (no PGG) and finally received one more dose of PGG (week 5). Adverse events and complete blood counts were evaluated. In addition, whole blood and serum was evaluated for the following at various time points post-infusion: PGG binding to immune cells (monocytes, neutrophils, B-cells, DC subsets), complement activation (C5a and Sc5b9), serum cytokine/chemokine levels, IgG ABA levels, flow cytometry of immune cells, circulating immune complex formation and Quantigene analysis of transcriptional profile. Table 1 lists each subject's pre-dose IgG ABA levels, PGG dose and whether they received premedications.

TABLE 1

| Cohort 1 (4 mg/kg PGG) | | | Cohort 2 (4 mg/ml PGG) | | | Cohort 3 | | |
| --- | --- | --- | --- | --- | --- | --- | --- | --- |
| subject | ABA IgG (μg/ml) | Pre-med | subject | ABA IgG (μg/ml) | Pre-med | subject | ABA IgG (μg/ml) | dose |
| 02 | 32.9 | No | 25 | 10.9 | No | 51 | 62.4 | 2 mg/kg |
| 04 | 35.7 | No | 29 | 10.5 | Yes | 52 | 21.9 | 2 mg/kg |
| 06 | 114.3 | No | 30 | 84.5 | Yes | 54 | 64.5 | 2 mg/kg |
| 07 | 143.7 | Yes | 32 | 11.8 | Yes | 55 | 56.2 | 4 mg/kg |
| 09 | 12.9 | Yes | 34 | 71.3 | No/Yes | 57 | 37.3 | 4 mg/kg |
| 10 | 183.2 | No | 37 | 10.8 | No | 58 | 34 | 4 mg/kg |
| 13 | 39 | Yes | 38 | 114.0 | Yes | 59 | 26.6 | 2 mg/kg |
| 16 | 29 | No | 39 | 12.3 | No | 60 | 25 | 2 mg/kg |
| 17 | 18.2 | Yes | 41 | 25.0 | Yes | 67 | 15 | 4 mg/kg |
| 18 | 30.7 | Yes | 43 | 33.5 | No | 68 | 26.1 | 4 mg/kg |
| 20 | 41.9 | Yes | 45 | 22.5 | Yes | 70 | 58.7 | 4 mg/kg |
| 22 | 87.9 | No | 47 | 34.4 | No | 71 | 14.6 | 2 mg/kg |

Biomarker research demonstrated differences among subjects in the ability of their neutrophils and monocytes to bind yeast soluble β-glucan. Binding of yeast soluble β-glucan to these cells correlated with the subjects' immunomodulatory response to yeast soluble β-glucan. Moreover, yeast soluble β-glucan binding to neutrophils and monocytes involves the presence of a specific level of natural anti-β-glucan antibodies. Biomarker assay methods to quantitatively measure anti-β-glucan IgG and IgM antibodies (ABAs) in patient serum samples are described in International Published Application Nos. WO2013165591A1 and WO2015084732A1. Cutoff levels for the biomarker assay identify subjects as biomarker positive and biomarker negative subgroups and these cutoff points correlate with binding, function, and clinical outcomes. Biomarker positive subjects have a better response to soluble β-glucan immunotherapies than biomarker negative subjects. Further evidence, however, shows that ABA levels also correlate with the immunopharmacodynamic (IPD) responses and adverse events of subjects that were administered soluble β-glucan. This finding allows for more precise dosing of subjects receiving soluble β-glucan immunotherapies.

IPD changes induced by yeast soluble β-glucan were evaluated in a Phase I healthy donor trial, which included three cohorts of 12 healthy human volunteers aged 18-65 years. In Cohort 1, subjects were administered a single dose of 4 mg/kg yeast soluble β-glucan by IV infusion over 2-3 hours. In Cohort 2, subjects were administered 4 mg/kg PGG by IV infusion over 2-3 hours once weekly for 3 weeks. Half of the subjects received premedications which included low dose corticosteroids (4 mg of dexamethasone, PO) and low-dose H1 antagonists (50 mg diphenhydramine).

In Cohort 3, subjects received either 2 mg/kg PGG or 4 mg/kg PGG by IV infusion over 1-2 hours. The subjects were administered either dose of PGG once weekly for 2

Subjects were stratified/classified into subgroups based on pre-infusion ABA levels. ABA cutoff levels were selected based on prior studies and are only exemplary. Classification may include only 2 subgroups based on an IgG ABA cutoff level of 15 μg/ml, 20 μg/ml, 25, μg/ml, 30 μg/ml, 35 μg/ml, 40 μg/ml, 45 μg/ml or 50 μg/ml. Classification may also include 3, 4, 5 or more subgroups with each subgroup corresponding to a specific IgG ABA level range. For example, a 3 subgroup classification may include a Low-ABA subgroup encompassing ABA level ranges of <15 μg/ml, <20 μg/ml, <25 μg/ml or <30 μg/ml, a Mid-ABA subgroup encompassing a range having a low end ABA level of 20 μg/ml, 25 μg/ml, 30 μg/ml, 35 μg/ml, 40 μg/ml or 45 μg/ml and a high end ABA level of 30 μg/ml, 35 μg/ml, 40 μg/ml, 45 μg/ml, 50 μg/ml or 55 μg/ml, and a High-ABA subgroup encompassing ABA level ranges of >35 μg/ml, >40 μg/ml, >45 μg/ml, >50 μg/ml, >55 μg/ml, >60 μg/ml, >65 μg/ml or >70 μg/ml. As discussed in International Published Application No. WO2015084732A1, various ABA cutoff levels may be used for reasons such as differences in soluble β-glucan immunotherapy treatments and preferences regarding inclusiveness and exclusiveness of subgroups. Here, subjects whose ABA levels were less than 20 μg/ml were considered Low-ABA. Subjects with ABA levels between 20 μg/ml and 50 μg/ml were considered Mid-ABA. Subjects with ABA levels greater than 50 μg/ml were High-ABA. Serum and cellular IPD markers were analyzed pre-infusion, 15 minutes, 30 minutes and 1 hour post-infusion, end of infusion (EOI) and 1 hour, 2 hours, 3 hours, 4 hours, 24 hours, 48 hours and 168 hours after EOI. The results show the IPD changes induced by a single dose of PGG in subjects with different ABA levels.

Figure 1B:
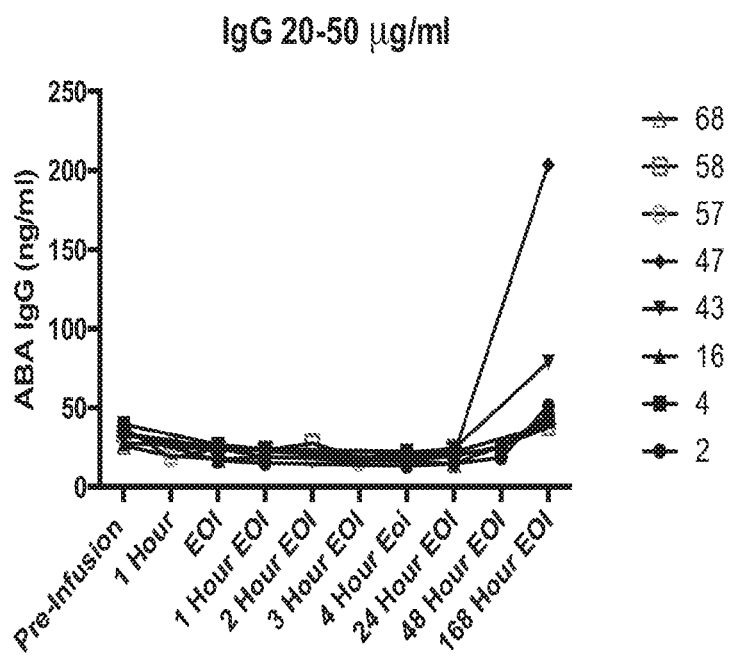
FIG. 1B. Anti-β-glucan antibody levels measured in serum of healthy human subjects classified as Mid-ABA which were intravenously administered PGG.
Figure 1C:
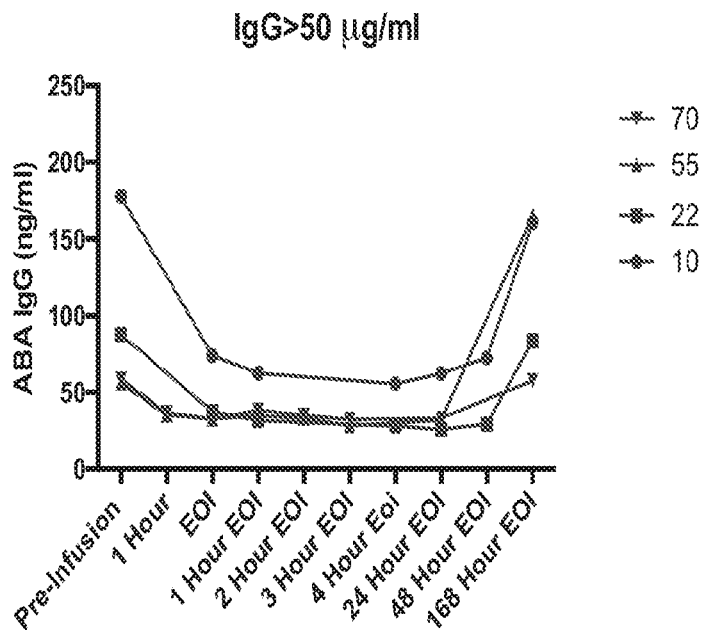
FIG. 1C. Anti-β-glucan antibody levels measured in serum of healthy human subjects classified as High-ABA which were intravenously administered. PGG.

FIG. 1 shows ABA level changes, measured by ELISA, for each subgroup. In panel A, ABA levels in Low-ABA subjects are essentially unaffected by PGG administration. In panel B, ABA levels in Mid-ABA subjects increased at 48 hours after the EOI. Lastly, in panel C, ABA levels in High-ABA subjects dropped during infusion with PGG and then rebounded about 48 hours EOI.

Figure 2A:
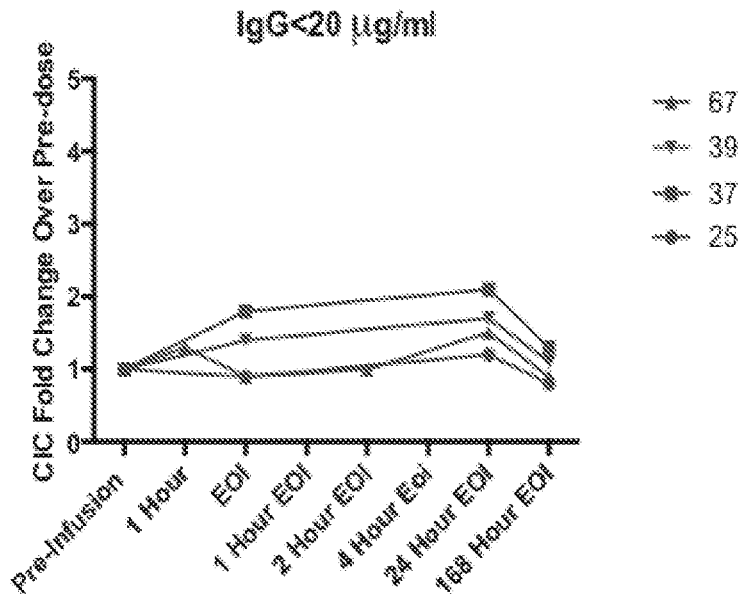
FIG. 2A. Circulating immune complex levels measured in serum of healthy human subjects classified as Low-ABA which were intravenously administered PGG.
Figure 2B:
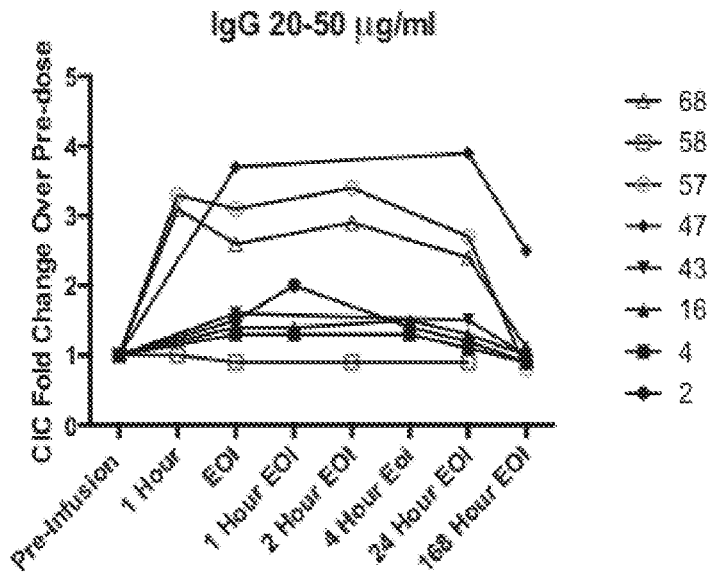
FIG. 2B. Circulating immune complex levels measured in serum of healthy human subjects classified as Mid-ABA which were intravenously administered PGG.
Figure 2C:
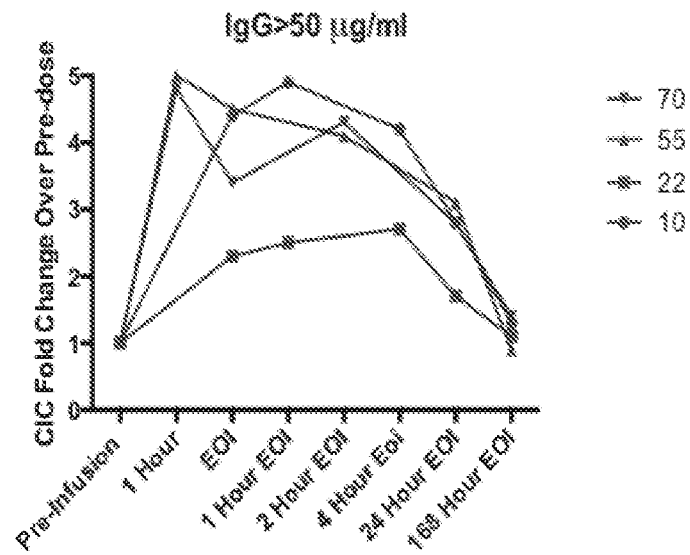
FIG. 2C. Circulating immune complex levels measured in serum of healthy human subjects classified as High-ABA which were intravenously administered PGG.

It was also found that increases in the level of circulating immune complexes (CIC) correlated with ABA levels, which is shown in FIG. 2. Total CIC formation was measured in serum by ELISA (Quidel). Panels A, B and C show little increase in CIC in Low-ABA subjects, a greater increase in CIC in Mid-ABA subjects and the highest increase in CIC in High-ABA subjects, respectively. The drop in ABA levels and concomitant increase in CIC were seen at the EOI.

Figure 3A:
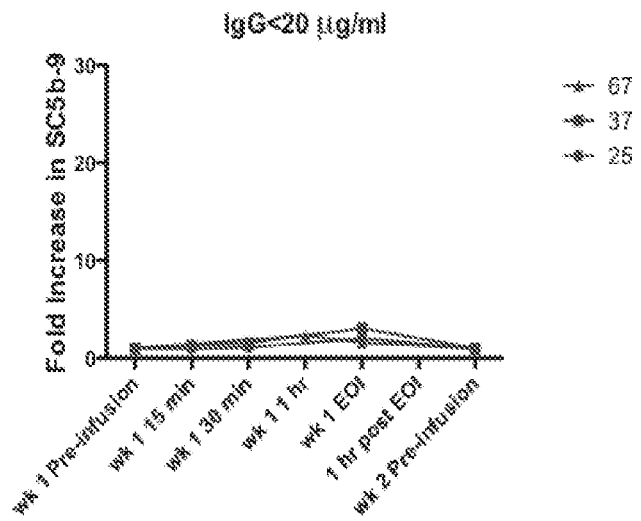
FIG. 3A. Complement activation (SC5b-9 levels) measured in plasma of healthy human subjects classified as Low-ABA which were intravenously administered PGG.
Figure 3B:
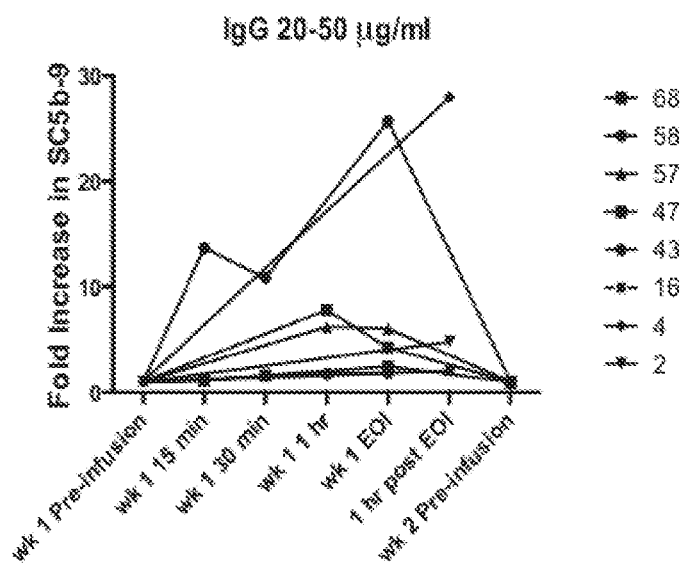
FIG. 3B. Complement activation (SC5b-9 levels) measured in plasma of healthy human subjects classified as Mid-ABA which were intravenously administered PGG.
Figure 3C:
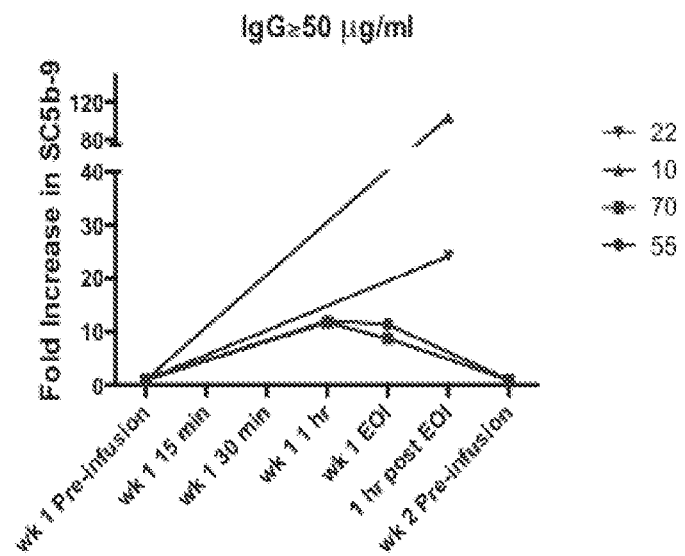
FIG. 3C. Complement activation (SC5b-9 levels) measured in plasma of healthy human subjects classified as High-ABA which were intravenously administered PGG.

Levels of complement activity, measured by ELBA (Quidel) in plasma, were determined by measuring complement activation products, C5a and SC5b-9. Levels were measured week 1 pre-infusion, 15 minutes, 30 minutes and 1 hour post-infusion, EOL 1 hour EOI and week 2 pre-infusion. The resulting SC5b-9 levels are shown in FIG. 3. Again, the levels of increase in complement activation correlated with ABA levels with levels peaking at EOI. The same results were obtained with C5a (data not shown).

Figure 4A:
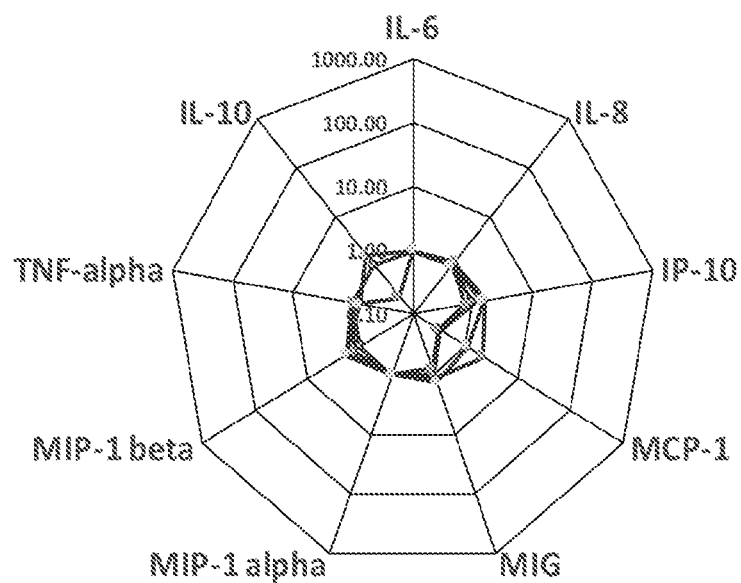
FIG. 4A. Cytokine/chemokine levels measured in serum of healthy human subjects classified as Low-ABA which were intravenously administered PGG. End of infusion relative to pre-dose values are plotted.
Figure 4B:
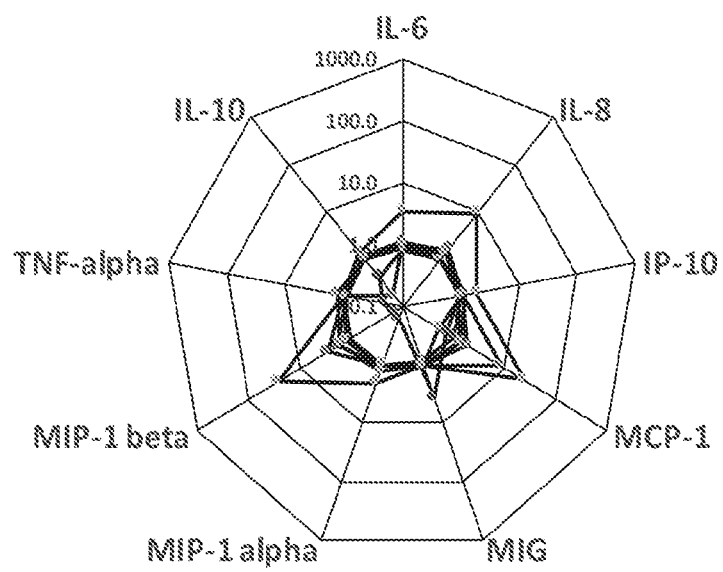
FIG. 4B. Cytokine/chemokine levels measured in serum of healthy human subjects classified as Mid-ABA which were intravenously administered PGG. End of infusion relative to pre-dose values are plotted.
Figure 4C:
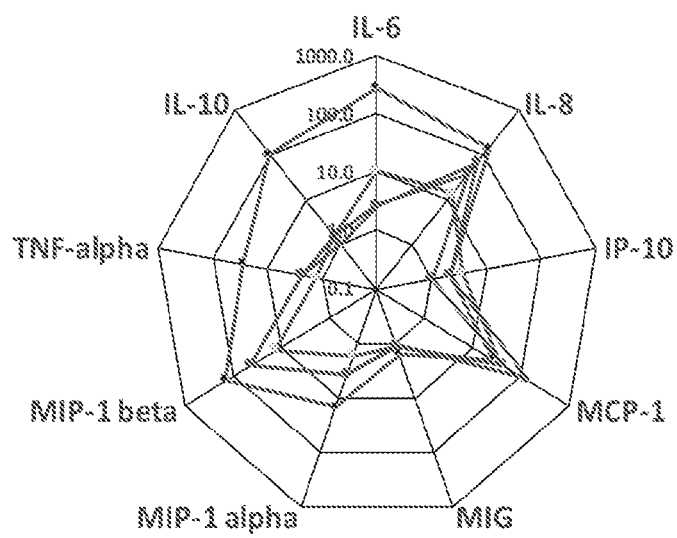
FIG. 4C. Cytokine/chemokine levels measured in serum of healthy human subjects classified as High-ABA which were intravenously administered PGG. End of infusion relative to pre-dose values are plotted.

Cytokine and chemokine serum levels were measured using Novex magnetic multiplex assay (Life Technologies) the Luminex XMAP technology. Increases, especially in IL-8 and MCP-1, from pre-dose values to the Eat, were consistently detected as shown in FIG. 4. Here again, the amount of increase in cytokine and chemokine levels correlated with ABA levels.

Figure 5:
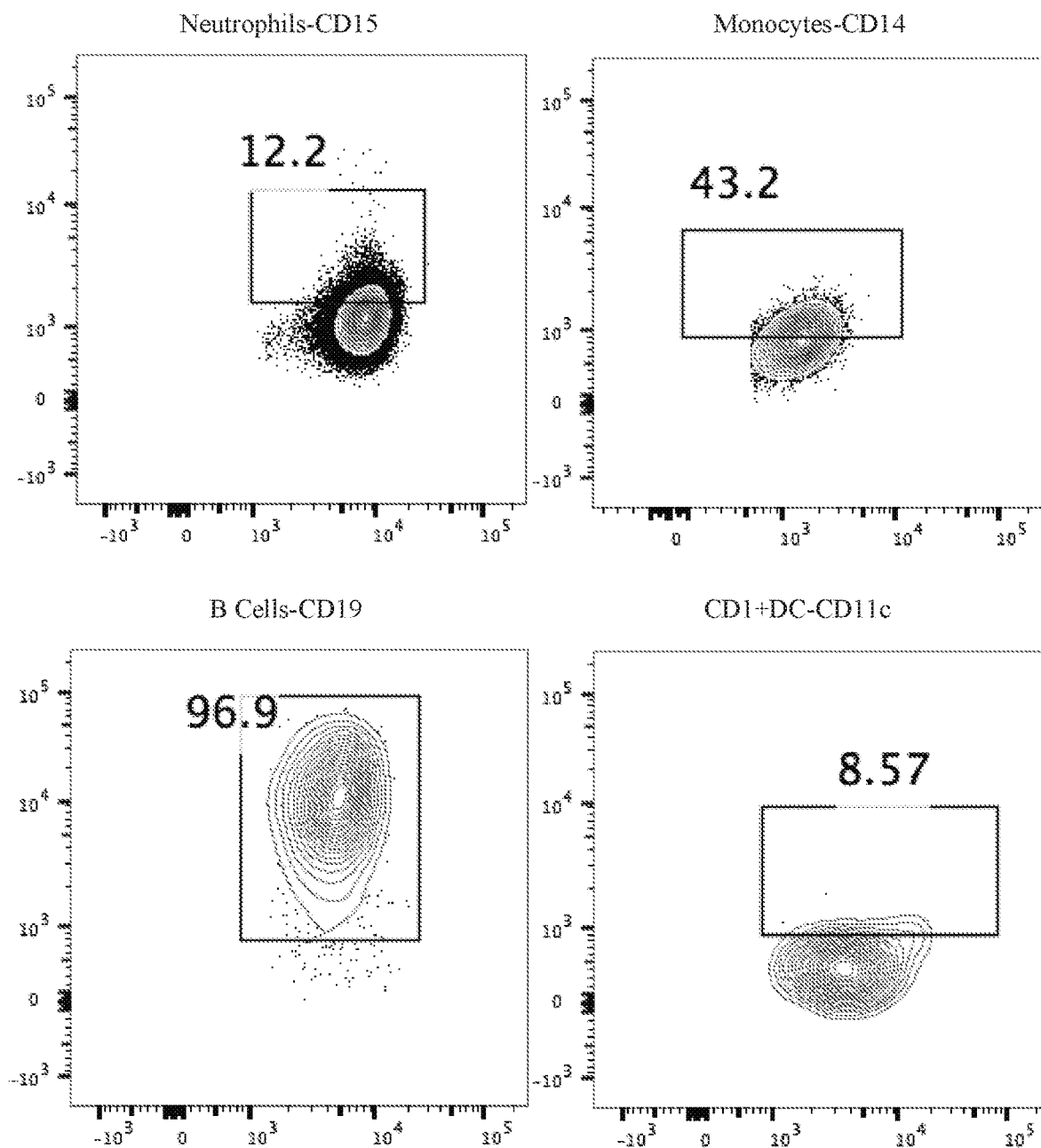
FIG. 5. In vivo immune cell binding assessed by flow cytometry from whole blood at the end of infusion of High-ABA subjects dosed with PGG Gates were set based on BMW staining (Anti-PGG MAb) on blood cells prior to infusion.

In vivo immune cell binding was assessed by flow cytometry from whole blood of subjects dosed with PGG at the EOI. Gates were set based on BFDPV staining (anti-PGG MAb) on blood cells prior to infusion. As shown in FIG. 5, PGG bound to neutrophils, monocytes, B cells and subsets of dendritic cells (DC).

Figure 6A:
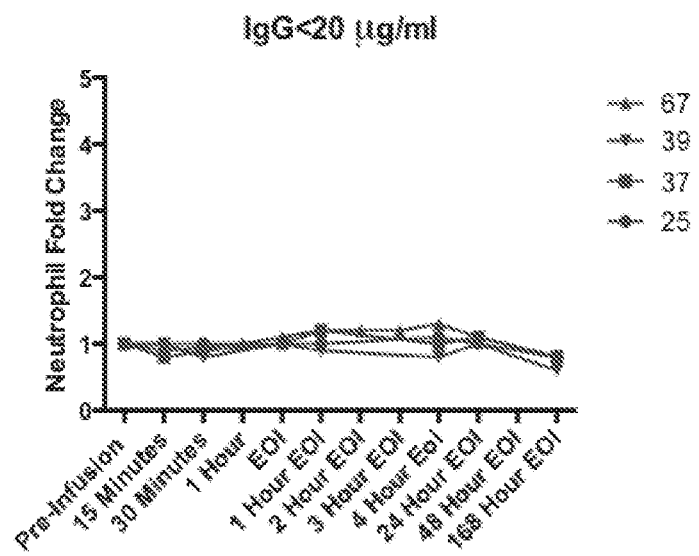
FIG. 6A. Cell mobilization measured by complete blood cell counts, plus differentials, from healthy human subjects classified as Low-ABA which were intravenously administered PGG. Neutrophil numbers only are represented.
Figure 6B:
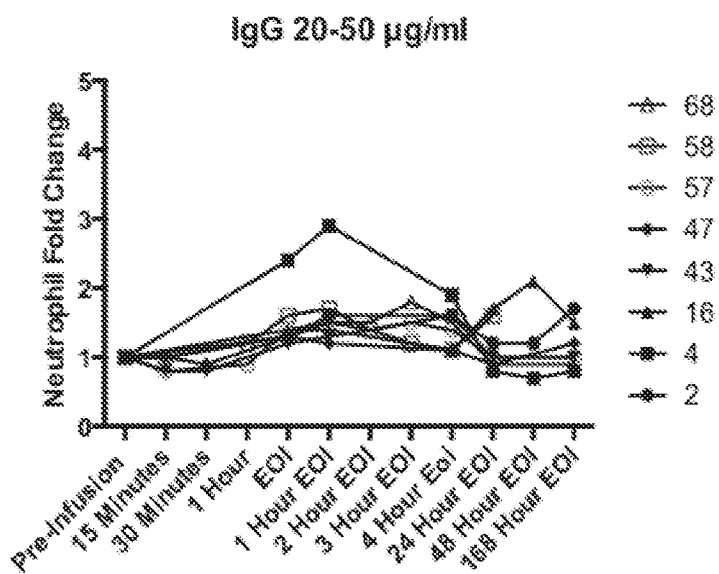
FIG. 6B. Cell mobilization measured by complete blood cell counts, plus differentials, from healthy human subjects classified as Mid-ABA which were intravenously administered PGG. Neutrophil numbers only are represented.
Figure 6C:
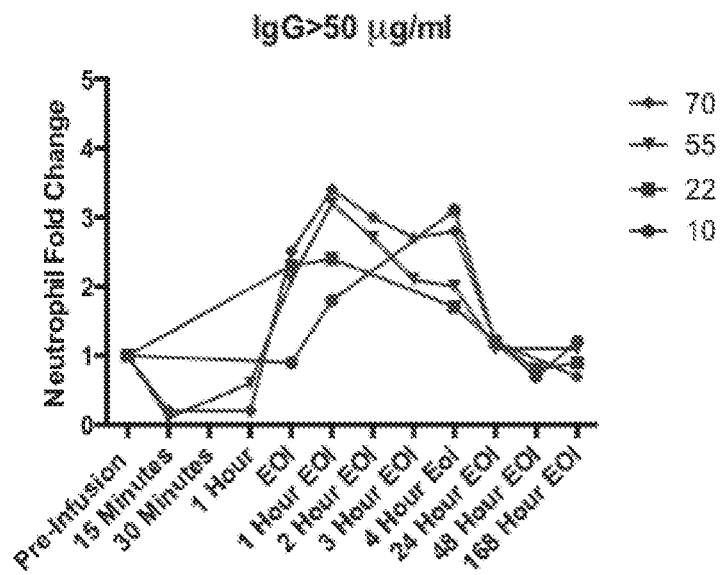
FIG. 6C. Cell mobilization measured by complete blood cell counts, plus differentials, from healthy human subjects classified as High-ABA which were intravenously administered PGG. Neutrophil numbers only are represented.

Cell mobilization was measured by complete blood cell counts, plus differentials. Only neutrophil numbers are shown, but monocyte and lymphocyte numbers were also collected. Like the other PDI responses, neutrophil and monocyte mobilization correlated with ABA levels. Specifically, as shown in FIGS. 6A-6C, a 2- to 3-fold increase in neutrophil and monocyte (data not shown) numbers were seen 4 hours post-infusion.

Figure 7:
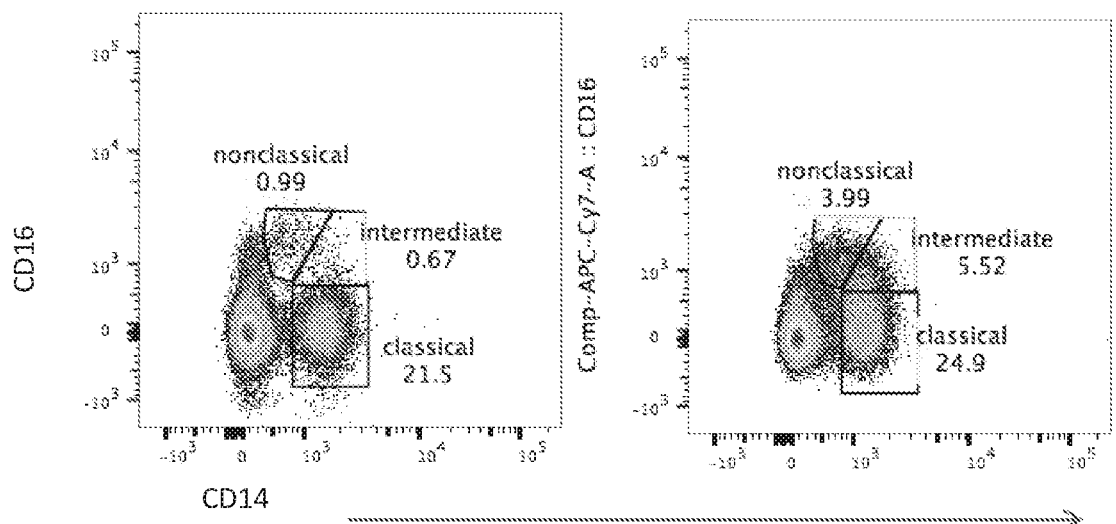
FIG. 7. Appearance of nonclassical/intermediate monocytes measured in the peripheral blood mononuclear cells of High-ABA subjects stained with indicating markers and analyzed by flow cytometry. Each of the populations were assessed for expression of activation markers CD86, ICAM-1, HLA-DR and PD-L1 24 hours after infusion.
Figure 7:
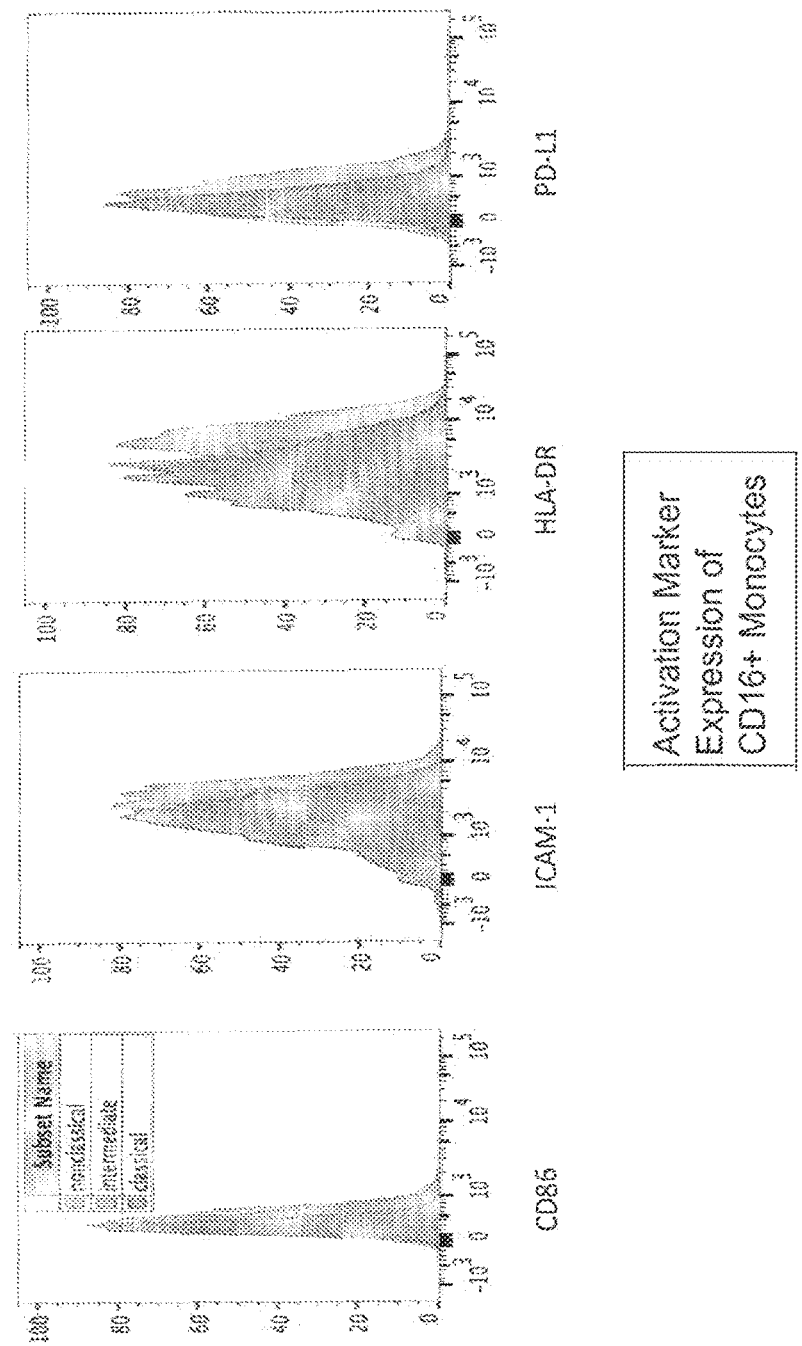

As shown in FIG. 7, 24 hrs after EOI, a population of intermediate monocytes expressing higher levels of the activation markers CD86, PD-L1 and HLA-DR was observed. Here, PBMC were stained with indicating markers and analyzed by flow cytometry. Each of the populations were assessed for expression of activation markers CD86, ICAM-1, HLA-DR and PD-L1 24 hours after infusion. In addition, approximately one week post-infusion, increased switched memory B cells and plasmablasts were detected (data not shown).

Figure 8:
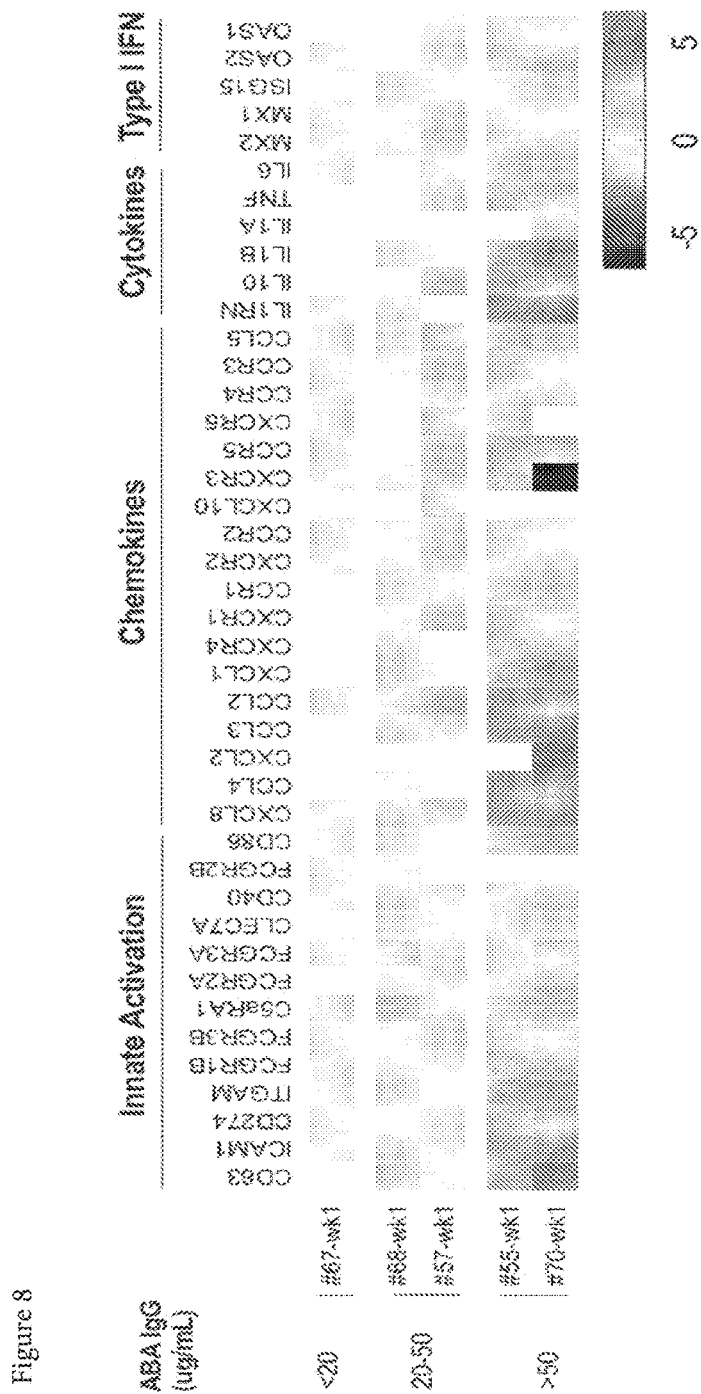
FIG. 8. Gene expression measured in blood of High-ABA subjects dosed with PGG (3 hr post-infusion vs. pre-dose levels).

Gene expression in blood of subjects dosed with PGG (3 hr post-infusion vs. pre-dose levels) are shown in FIG. 8. Whole blood was collected in PaxGene blood collection tubes (BD Biosciences) at various time points pre- and post-PGG administration. RNA was isolated and assayed by Quantigeneplex (Affymetrix) and the relative fold changes were log 2 transformed. Data presented are from subjects treated with PGG without premedications. Expression of innate immune activation marker genes was consistently increased in subjects with higher levels of ABA.

Thus, changes in IPD responses induced by PGG administration are dependent on ABA levels. However, low-ABA subjects show very little to no changes in responses.

Figure 9:
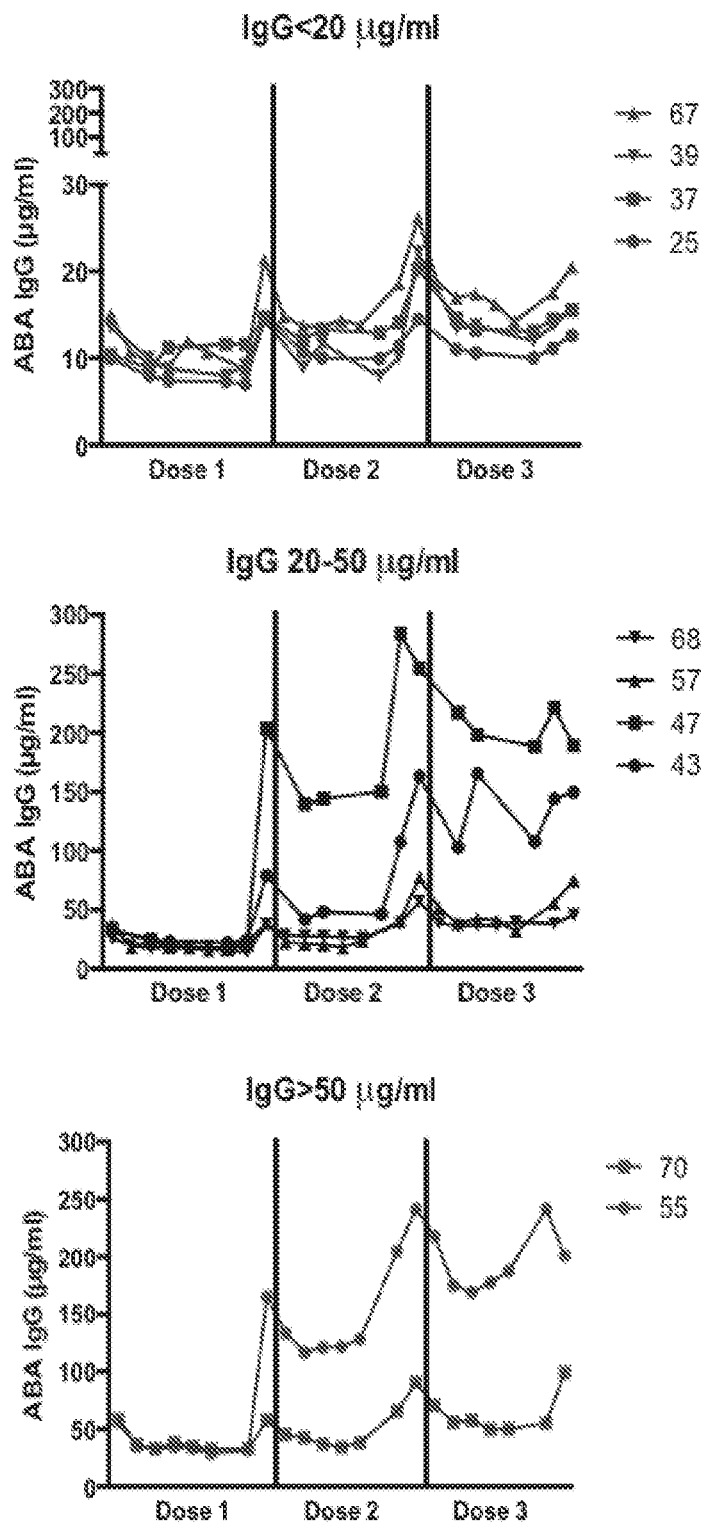
FIG. 9. Anti-β-glucan antibody levels measured in serum from Low-ABA, Mid-ABA and High-ABA subjects at various time points before and after a single dose (Cohort 1) or multiple weekly doses (Cohorts 2 and 3) of PGG infusion.

ABA levels were then followed in subjects through single and multiple doses of PGG. ABA levels were measured in serum by ELISA, and subjects were placed in subgroups based on pre-infusion ABA levels: Low-ABA (<20 µg/mL), Mid-ABA (20-50 µg/mL) or High-ABA (>50 µg/mL). Whole blood or serum was drawn from the subjects at various time points before and after a single dose (Cohort 1) or multiple weekly doses (Cohorts 2 and 3) of PGG infusion. The results, shown in FIG. 9, indicate that multiple doses of PGG can increase ABA levels for some subjects. In some cases, such as shown for subject 67 in the Low-ABA subgroup, the increase may lead to a change in subgroup (Low-ABA to Mid-ABA).

Figure 10:
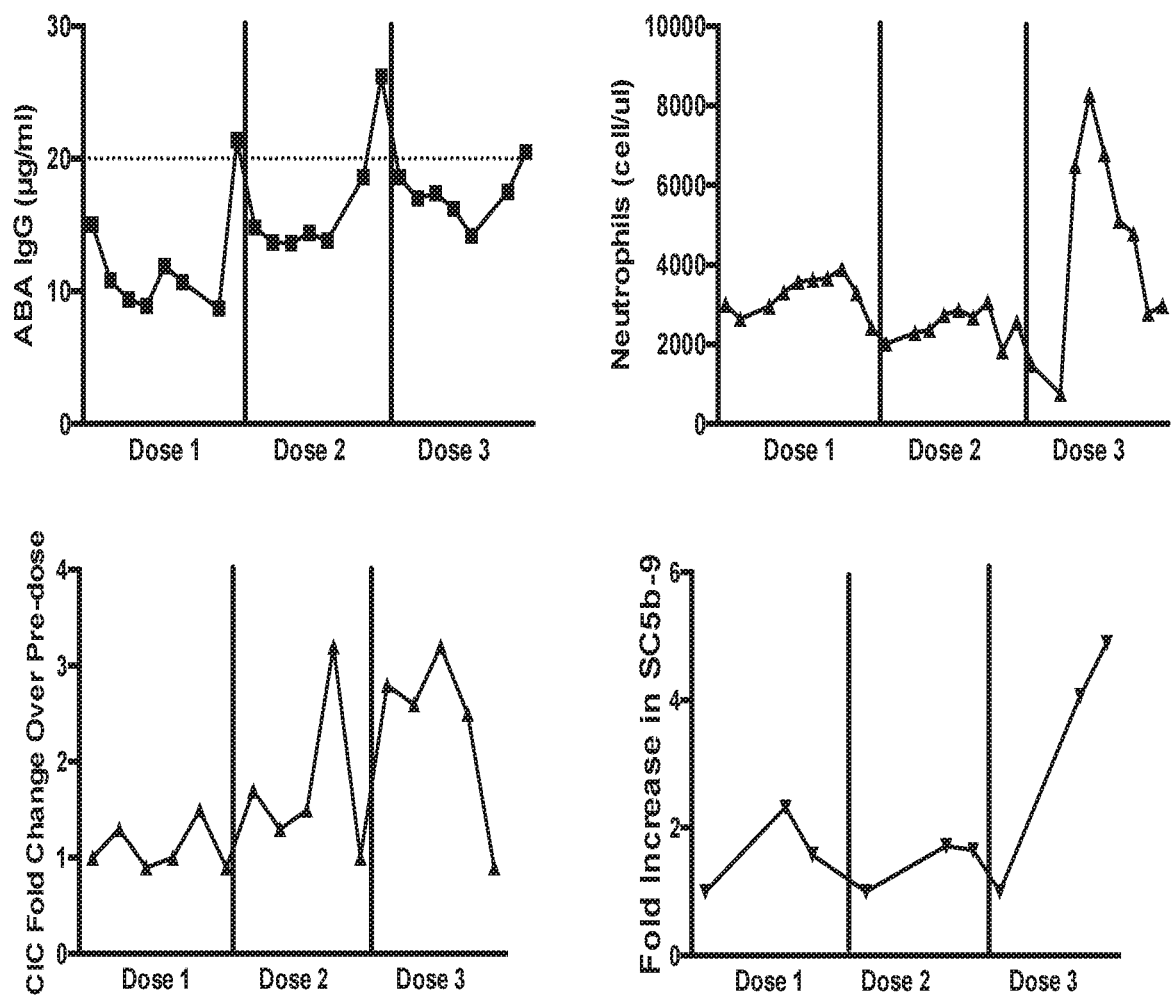
FIG. 10. Anti-β-glucan antibody levels, circulating immune complex levels, monocyte mobilization levels, complement activation levels and fold increase in cytokines/chemokines and gene expression 3 hours post-infusion were measured and one individual (subject 67), is shown illustrating a subject that converted from Low-ABA to Mid-ABA.
Figure 10:
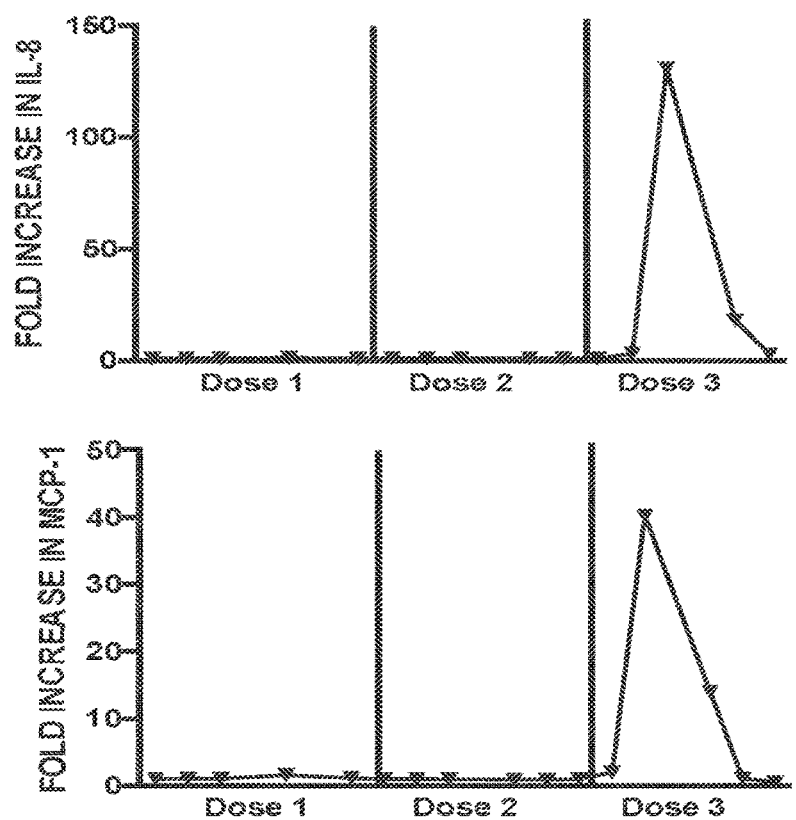
Figure 10:
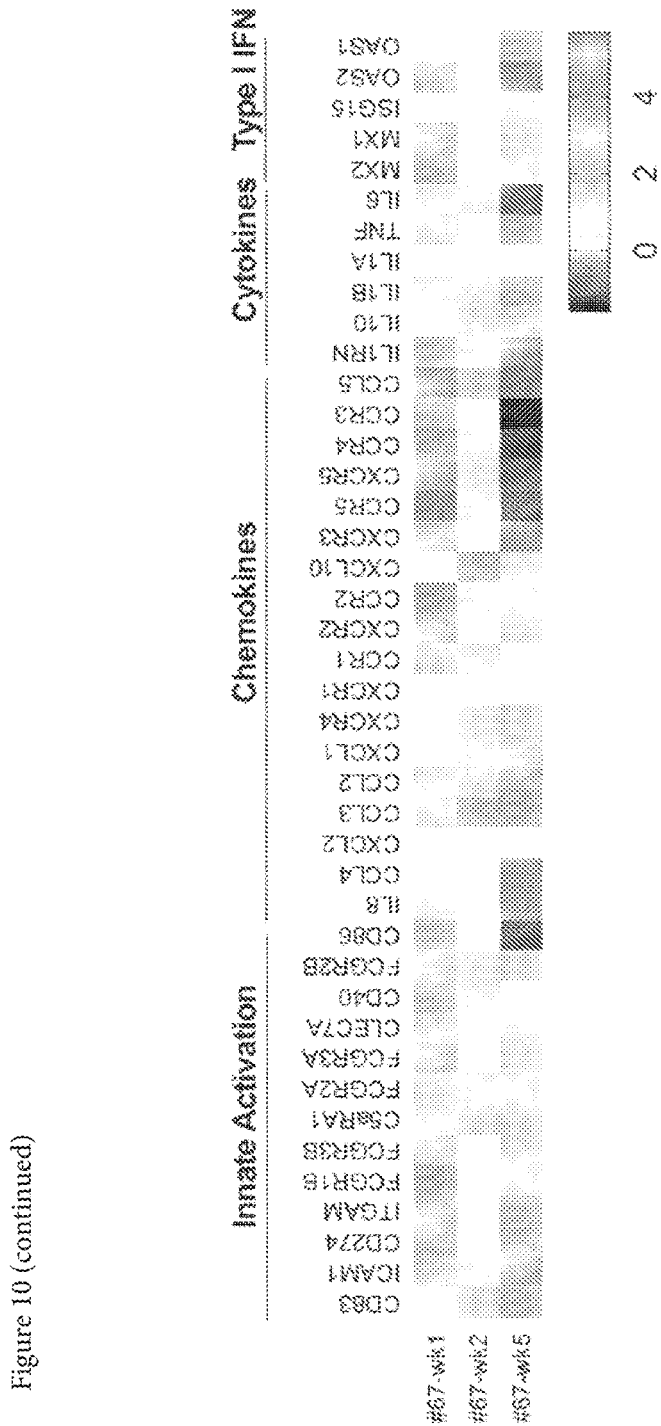

The increase in ABA levels and change in subgroup classification also induced IPD response changes consistent with the new classification. ABA, CIC, monocyte mobilization, complement activation, fold increase in cytokines/chemokines and gene expression (3 hours post-infusion) were measured and the results for one illustrative individual (subject 67) that converted from Low-ABA to Mid-ABA are shown in FIG. 10. Thus, in one embodiment of the invention, where a subject is identified as Low-ABA, the subject may be administered multiple doses of PGG to elevate ABA levels such that the subject is then identified as Mid-ABA. The subject would then adequately respond to soluble β-glucan immunotherapy.

Adverse events were evaluated for subjects after a single dose of IV PGG. Table 2 lists ABA levels and adverse events for subjects that had not received premedication prior to PGG infusion.

TABLE 2

| S/N | Age | Gender | ABA Screening | Pre-dose | Adverse Events (CTCAE grade) |
|---|---|---|---|---|---|
| 025 | 64 | M | 11.3 | 9.9 | None |
| 037 | 29 | M | 11.3 | 10.4 | None |
| 039 | 50 | M | 13.3 | 13.6 | Gr 1 headache |
|  |  |  |  |  | Gr 1 drowsiness |
| 067 | 31 | M | 17.7 | 15.0 | Gr 1 LE stiffness |
| 047 | 63 | M | 28.5 | 33.6 | None |
| 068 | 27 | F | 28.5 | 26.1 | None |
| 016 | 21 | F | 30.3 | 27.6 | Gr 1 headache |
| 002 | 19 | F | 34.2 | 34.4 | None |
| 058* | 52 | M | 35.9 | 34.0 | Gr 1 dysuria (delayed) |
|  |  |  |  |  | Gr 2 myalgia (delayed) |
|  |  |  |  |  | Gr 2 arthralgia (delayed) |
| 043 | 30 | F | 38.4 | 32.6 | Gr 2 headache |
| 057 | 55 | F | 39.2 | 37.3 | Gr 1 diarrhea |
| 004 | 33 | M | 41.5 | 39.7 | None |
| 055 | 64 | M | 66.2 | 56.2 | Gr 1 nausea |
|  |  |  |  |  | Gr 1 flushing |
|  |  |  |  |  | Gr 2 chest pressure |
|  |  |  |  |  | Gr 2 dyspnea |
|  |  |  |  |  | Gr 2 low back pain |
|  |  |  |  |  | Gr 2 headache (delayed) |
|  |  |  |  |  | Gr 2 back pain (delayed) |
|  |  |  |  |  | Gr 2 neck/shoulder pain (delayed) |
| 070 | 26 | M | 68.7 | 58.7 | Gr 1 headache |
| 034 | 31 | F | 78.4 | 68.0 | Gr 1 chest pressure |
|  |  |  |  |  | Gr 1 warm sensation |
|  |  |  |  |  | Gr 1 light headedness |
|  |  |  |  |  | Gr 1 nausea |
|  |  |  |  |  | Gr 1 hand paresthesia |
|  |  |  |  |  | Gr 2 chills |
|  |  |  |  |  | Gr 3 headache |
| 022 | 26 | M | 100.7 | 87.8 | Gr 1 chest pressure |
|  |  |  |  |  | Gr 1 light headedness |
|  |  |  |  |  | Gr 1 abdominal cramping |
|  |  |  |  |  | Gr 2 myalgia |
| 006 | 34 | M | 132.5 | 127 | Gr 1 chills |
|  |  |  |  |  | Gr 2 nausea/emesis |
|  |  |  |  |  | Gr 2 chest pressure |

TABLE 2-continued

| | | | ABA | | Adverse Events |
|---|---|---|---|---|---|
| S/N | Age | Gender | Screening | Pre-dose | (CTCAE grade) |
| 010 | 48 | M | 158.9 | 177.9 | Gr 1 back pain |
| | | | | | Gr 2 chest pressure |
| | | | | | Gr 2 nausea |

*Subject developed delayed symptoms of generalized arthralgia and myalgia with elevated C-reactive protein and was later determined to have had elevated pre-dose circulating immune complex levels.

The evaluation showed that infusion reaction-related adverse events (CARPA; complement-activation related pseudoallergy) are limited to infusion related reactions and observed in some, but not all, subjects with ABA levels>20 ug/ml. In addition, more adverse events occurred as ABA levels increased.

Figure 11A:
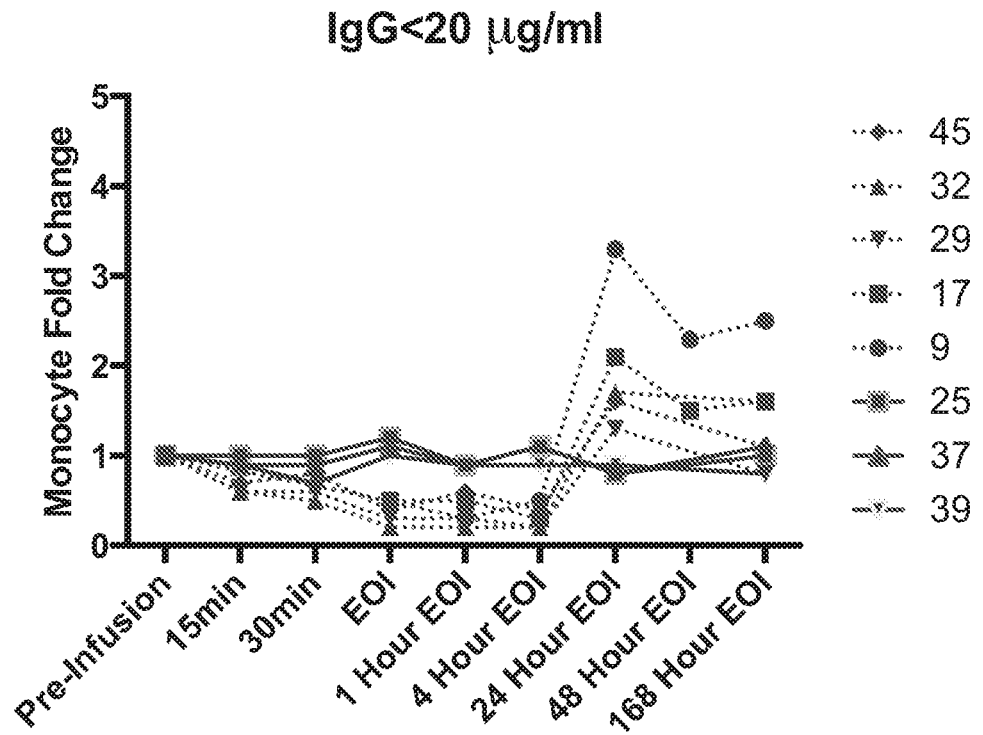
FIG. 11A. Monocyte mobilization measured by complete blood counts at various times before and after PGG administration in Low-ABA subgroup.

The effect of premedications on IPD responses was also evaluated. Whole blood or serum was drawn from subjects at various time points before and after a single dose (Cohort 1) or multiple weekly doses (Cohorts 2 and 3) of PGG infusion. Subjects were subgrouped by ABA levels: Low-ABA (<20 µg/mL), Mid-ABA (20-50 µg/mL) or High-ABA (>50 µg/mL). As shown in FIG. 11A, differences in monocyte mobilization were observed between Low-ABA subjects without premedications (filled lines) and Low-ABA subjects administered premedications (dashed lines).

Figure 11B:
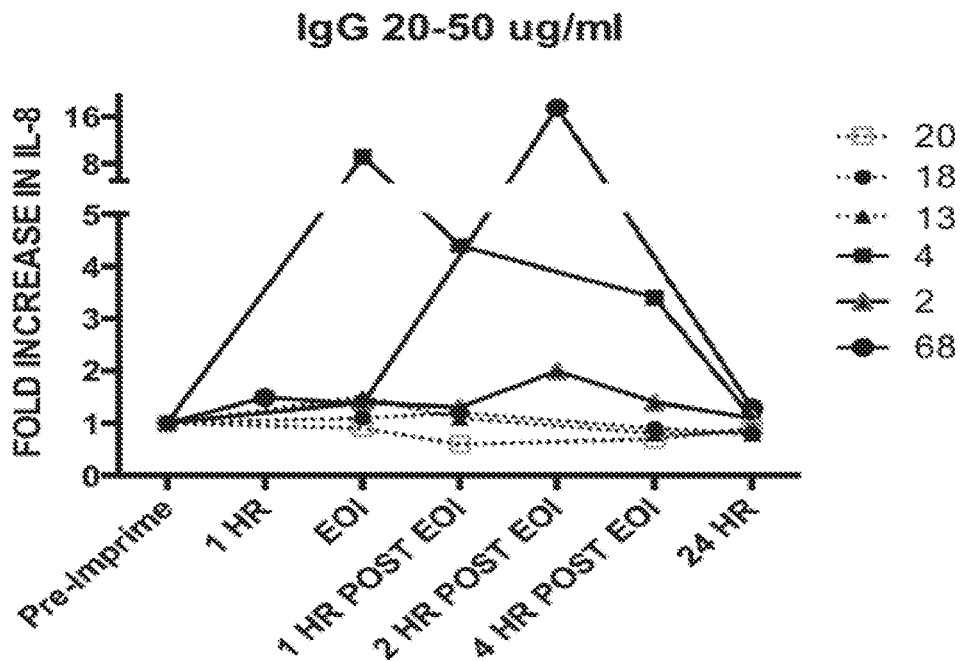
FIG. 11B. Cytokine production (fold IL-8 over pre-dose levels) measured in serum at various times before and after PGG administration in Mid-ABA and High-ABA subgroups.
Figure 11B:
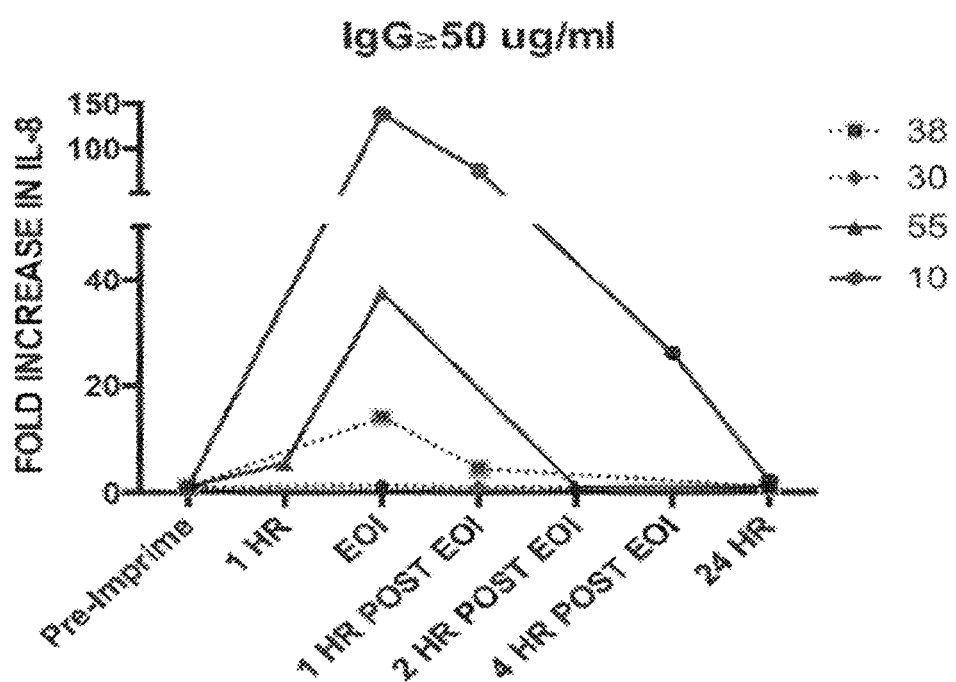

In addition, premedications (dashed lines) dampened PGG-mediated cytokine induction in Mid-ABA and High-ABA subjects. FIG. 11B shows the fold IL-8 production over pre-dose levels in subjects with premedications (dashed lines) and without premedications (filled lines).

Figure 12:
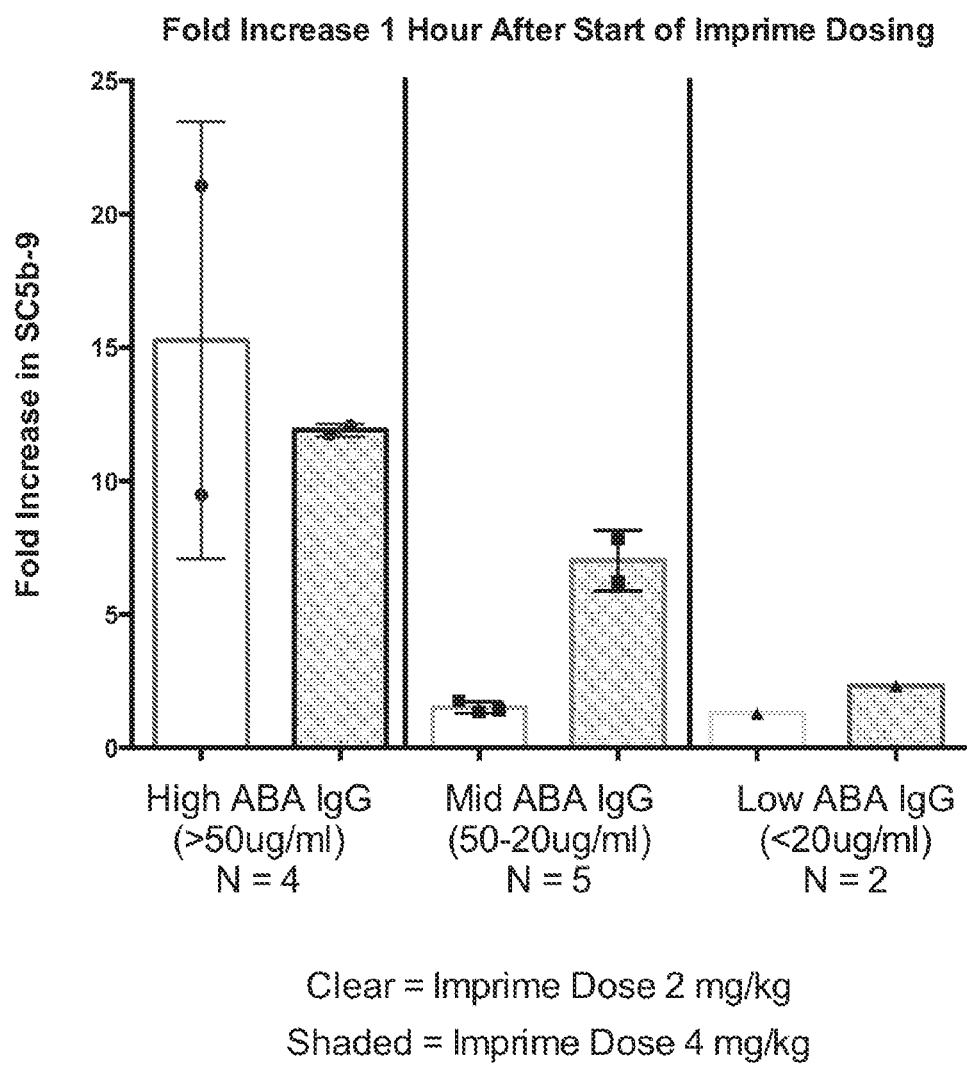
FIG. 12. Fold increase between pre-dose and 1 hour post-infusion in complement activation (SC5b-9 levels) measured in plasma of healthy human subjects classified as Low-ABA, Mid-ABA and High-ABA which were intravenously administered 2 mg/kg or 4 mg/kg PGG.
Figure 13:
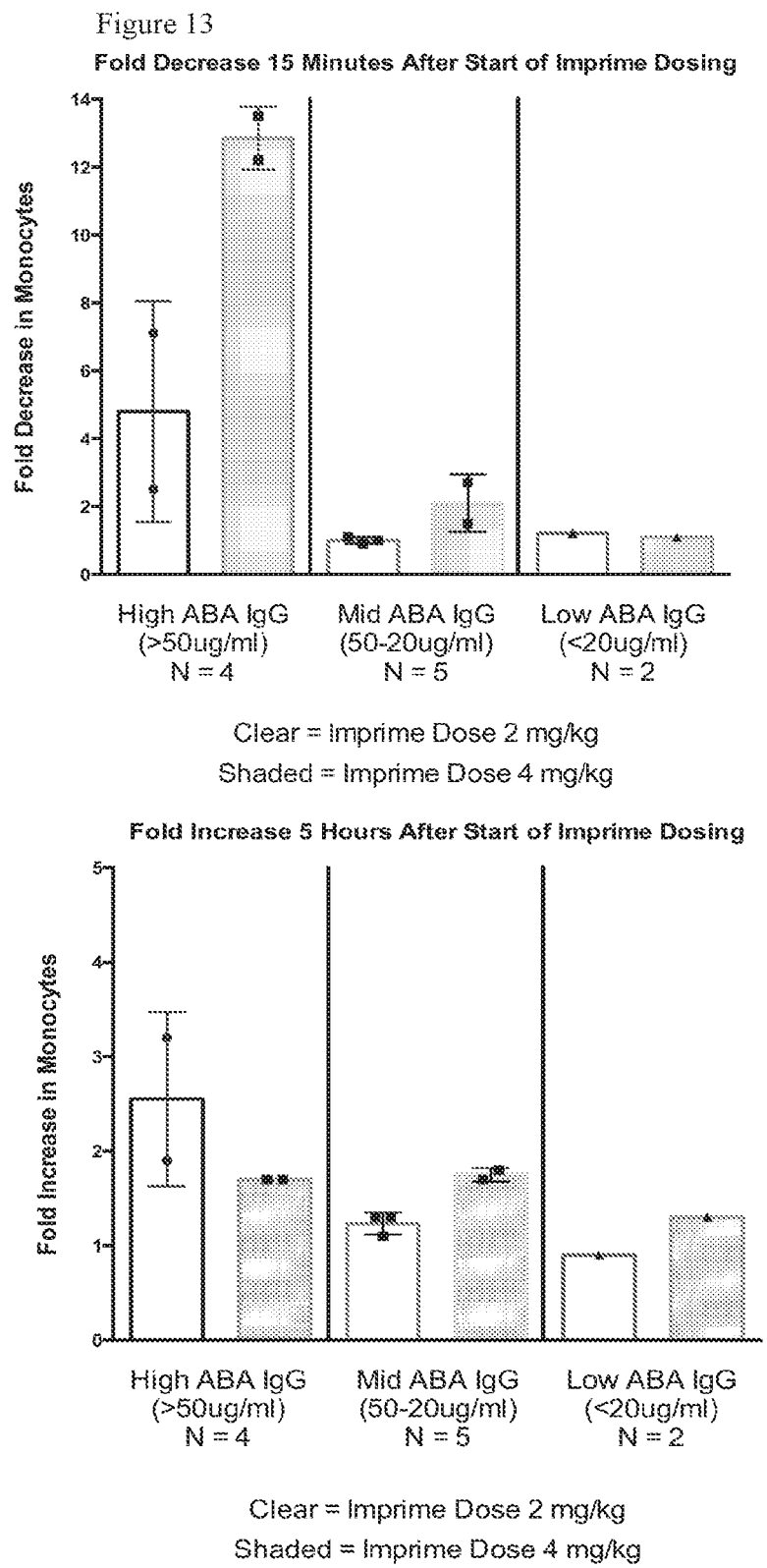
FIG. 13. Fold decrease between pre-dose and 15 minutes post-infusion in monocyte levels and fold increase between pre-dose and 5 hours post-infusion in monocyte levels measured in healthy human subjects classified as Low-ABA, Mid-ABA and High-ABA which were intravenously administered 2 mg/kg or 4 mg/kg PGG.
Figure 14:
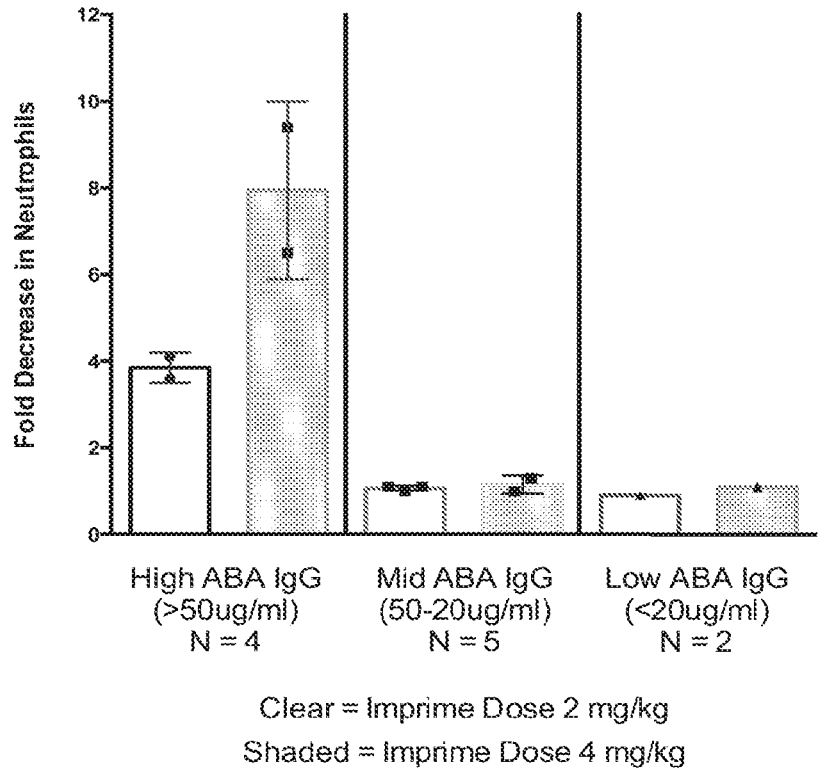
FIG. 14. Fold decrease between pre-dose and 15 minutes post-infusion in neutrophil levels and fold increase between pre-dose and 3 hours post-infusion in neutrophil levels measured in healthy human subjects classified as Low-ABA, Mid-ABA and High-ABA which were intravenously administered 2 mg/kg or 4 mg/kg PGG.
Figure 14:
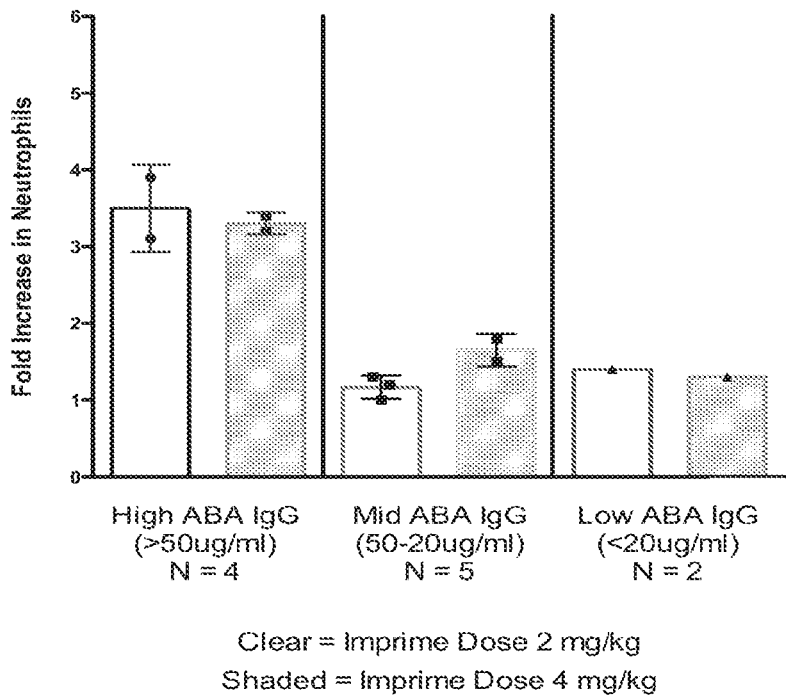
Figure 15:
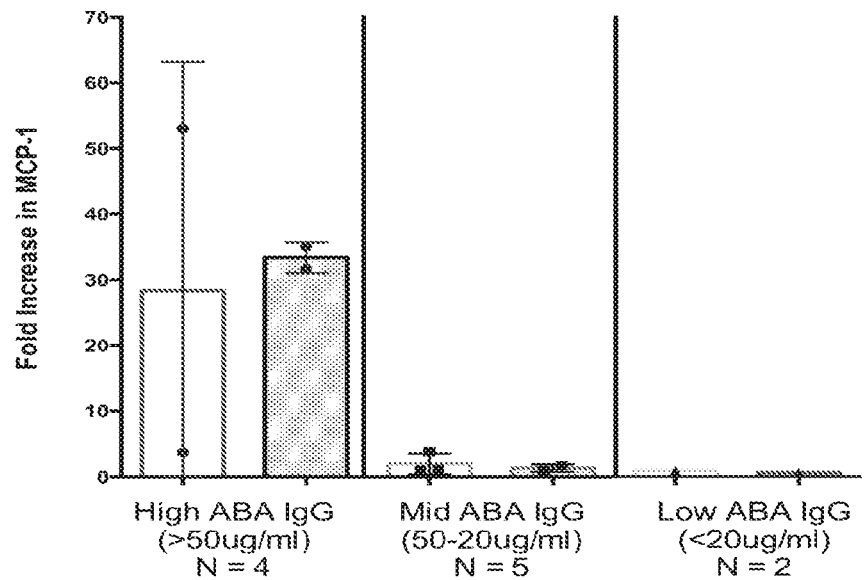
FIG. 15. Fold increase between pre-dose and 1 hour post-infusion in MCP-1 levels measured in serum of healthy human subjects classified as Low-ABA, Mid-ABA and High-ABA which were intravenously administered 2 mg/kg or 4 mg/kg PGG. Results of 3 experiments.
Figure 15:
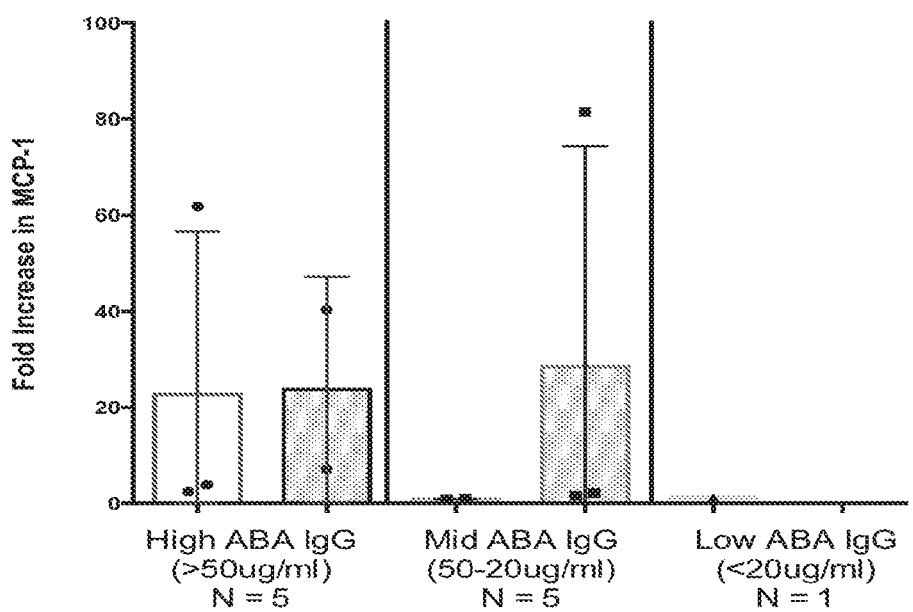
Figure 15:
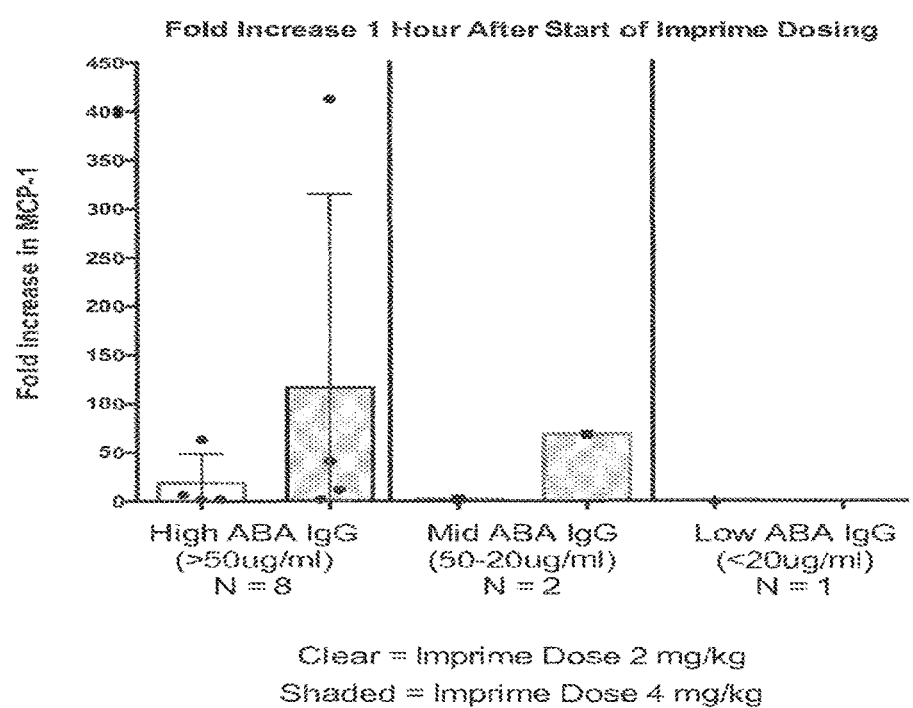

Importantly, PGG-driven IPD responses were found to be dose-dependent. IPD responses were compared between subjects within subgroups administered doses of either 2 mg/kg and 4 mg/kg PGG. The results comparing SC5b-9 (complement activation) are shown in FIG. 12. The results comparing monocyte mobilization are shown in FIG. 13. The results comparing neutrophil mobilization are shown in FIG. 14. The results comparing cytokine production (MCP-1) are shown in FIG. 15. Taken together, these results show that 2 mg/kg and 4 mg/kg dose-induced IPD responses were similar in subjects with ABA>50 µg/ml. Subjects with mid ABA levels (20 µg/ml-50 µg/ml) showed minimal response to the 2 mg/kg PGG dose but responded much better (on par with High-ABA subjects) to the 4 mg/kg PGG dose. Therefore, an effective dose of PGG for Mid-ABA subjects is higher than an effective dose of PGG for High-ABA subjects. This is beneficial to High-ABA subjects because with a lower PGG dose, they will experience fewer adverse events.

These doses are exemplary and other soluble β-glucan doses may be utilized depending on other factors, such as the specific disease being treated, the specific soluble β-glucan used, other drugs being administered, etc. The soluble β-glucan dose range is about 0.5 mg/kg to about 6 mg/kg including 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg and 6.0 mg/kg.

Importantly, because the IPD responses correlate with ABA levels, IPD levels may also be utilized to classify subjects into subgroups.

An important aspect of drug development is deriving appropriate dose strategies that provide maximum efficacy while minimizing adverse events. Dose strategies involve pre-dosing and administration timing as well as effective amounts. It is also more economically sound because subjects are not given more drug than necessary for treatment. It is shown here that ABA levels and/or IPD responses are useful in determining proper dosing levels for subjects undergoing soluble β-glucan immunotherapy.

As stated above, another aspect of deriving appropriate dose strategies involves the timing of administration. To this end, PGG-driven IPD responses were also found to be dependent on the length of interval between soluble β-glucan doses. Thus, changing the interval between soluble β-glucan administration provides a means of regulating IPD responses to enhance or increase the efficacy of immunotherapy.

Turning back to FIG. 3, the concept can be illustrated by the increase and decrease in SC5b-9 upon IV administration of soluble β-glucan. Panels B and C show that subjects with high enough ABA levels had significant increases in SC5b-9 that peaked at EOI, but those levels returned to baseline by pre-infusion week 2. Thus, upon a second dose of soluble β-glucan at week 2, one would expect to see the acute increase in SC5b-9 repeated. In this example, the generation of this acute SC5b-5 response can be repeated weekly during the course of treatment which may increase the efficacy of certain immunotherapies. A similar IPD response in CIC is shown in FIG. 2.

Figure 16:
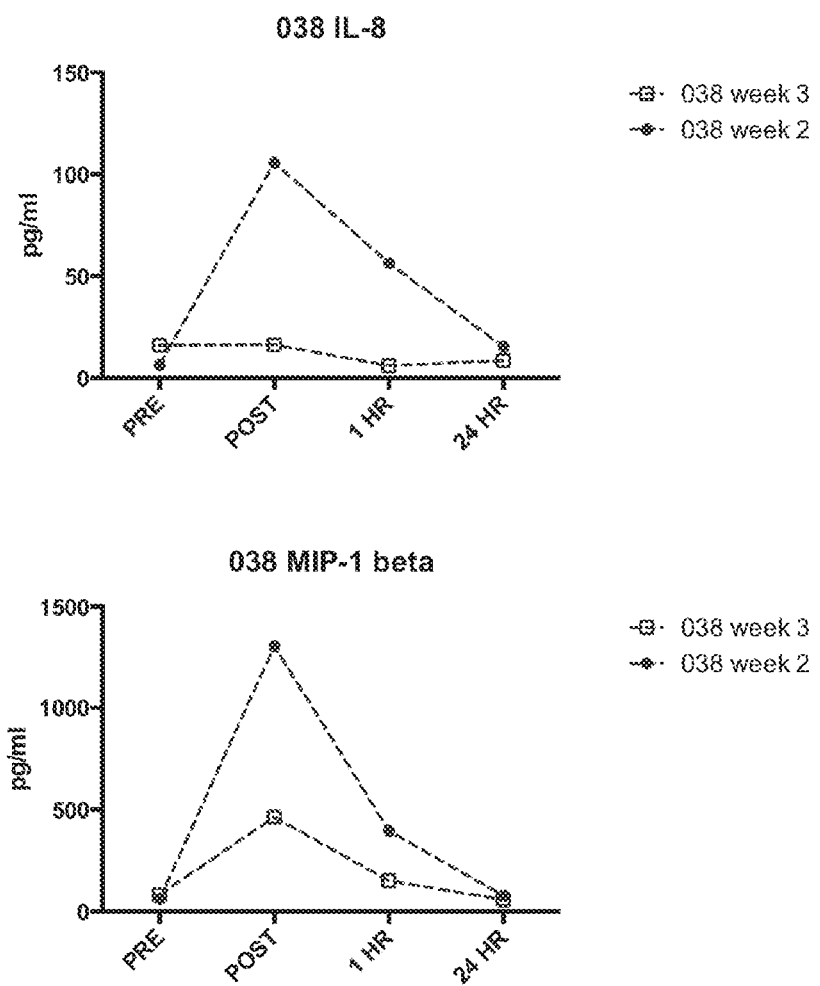
FIG. 16. A subject's IL-8, MCP-1 and MIP-1β levels measured at time points from pre-infusion to 24 hrs. post-infusion for week 2 and week 3.
Figure 16:
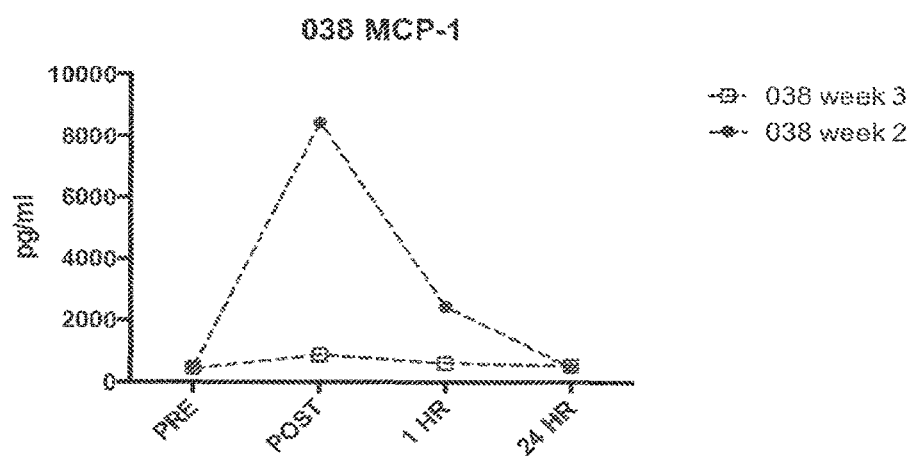
Figure 17:
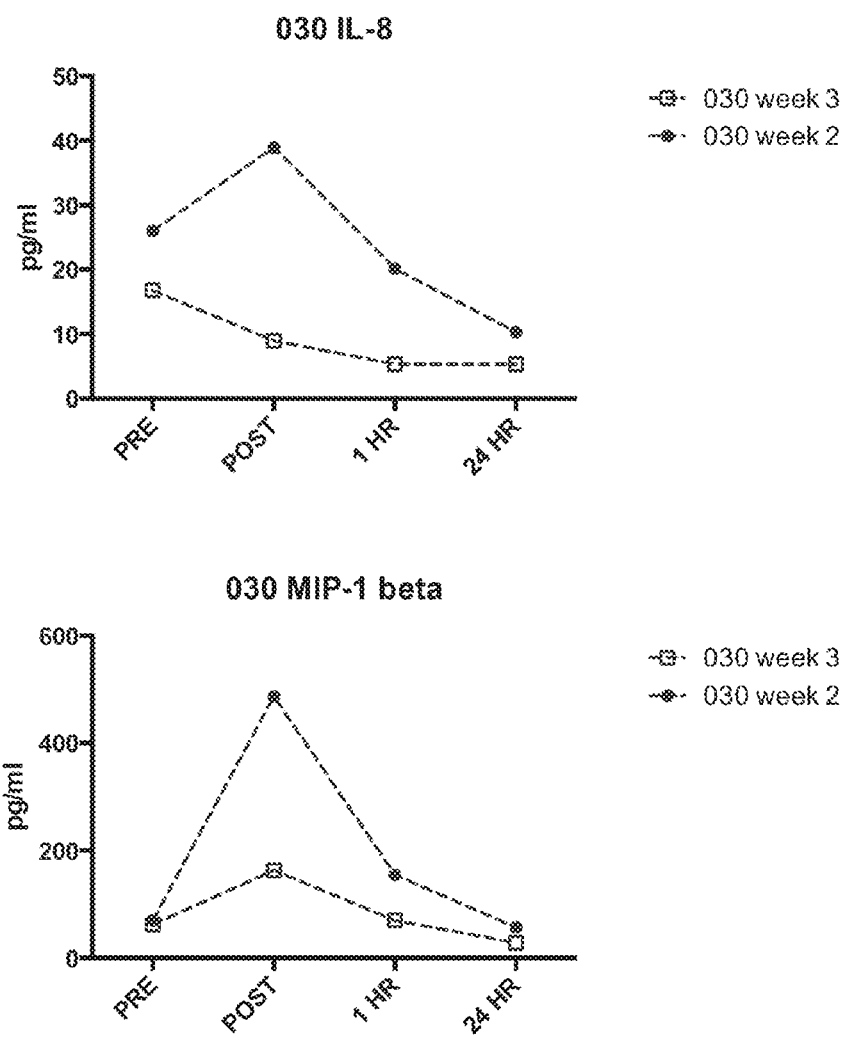
FIG. 17. A subject's IL-8, MCP-1 and MIP-1β levels measured at time points from pre-infusion to 24 hrs. post-infusion for week 2 and week 3.
Figure 17:
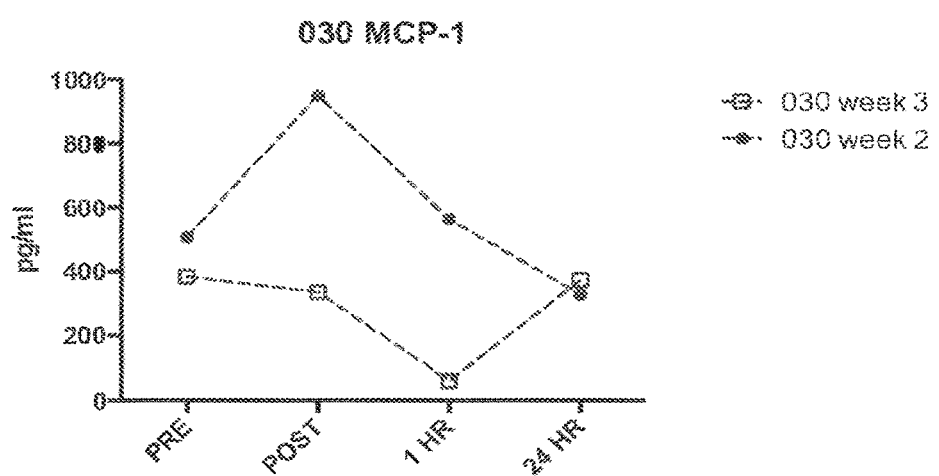

For some IPD responses, however, the interval between soluble β-glucan doses must be increased in order to repeat the acute IPD response. FIGS. 16 and 17 show levels of IL-8, MCP-1 and MIP-1 of two High-ABA subjects Pre-, Post-, 1 hr. post- and 24 hrs. post-infusion from two consecutive cycles of treatment. The cytokine levels were compared between week 2 dosing and week 3 dosing. As shown in the graphs, the an acute IPD response was seen after the week 2 infusion but was not seen after the week 3 infusion. This indicates that in order to repeat the acute response over the course of treatment, the interval or amount of time between administration of the remaining soluble β-glucan doses must be more than one week. Repeating acute IPD responses could enhance the efficacy of the subject's immunotherapy.

Increasing the time between soluble β-glucan doses may not only promote repeated acute IPD responses but also enhance acute IPD responses, which may increase the effectiveness of soluble β-glucan therapy. Subjects in Cohort 3, as described above, were administered a dose of PGG once weekly for 2 weeks, then given a 2 week wash out (no PGG) and finally received one more dose of PGG (week 5).

Figure 18:
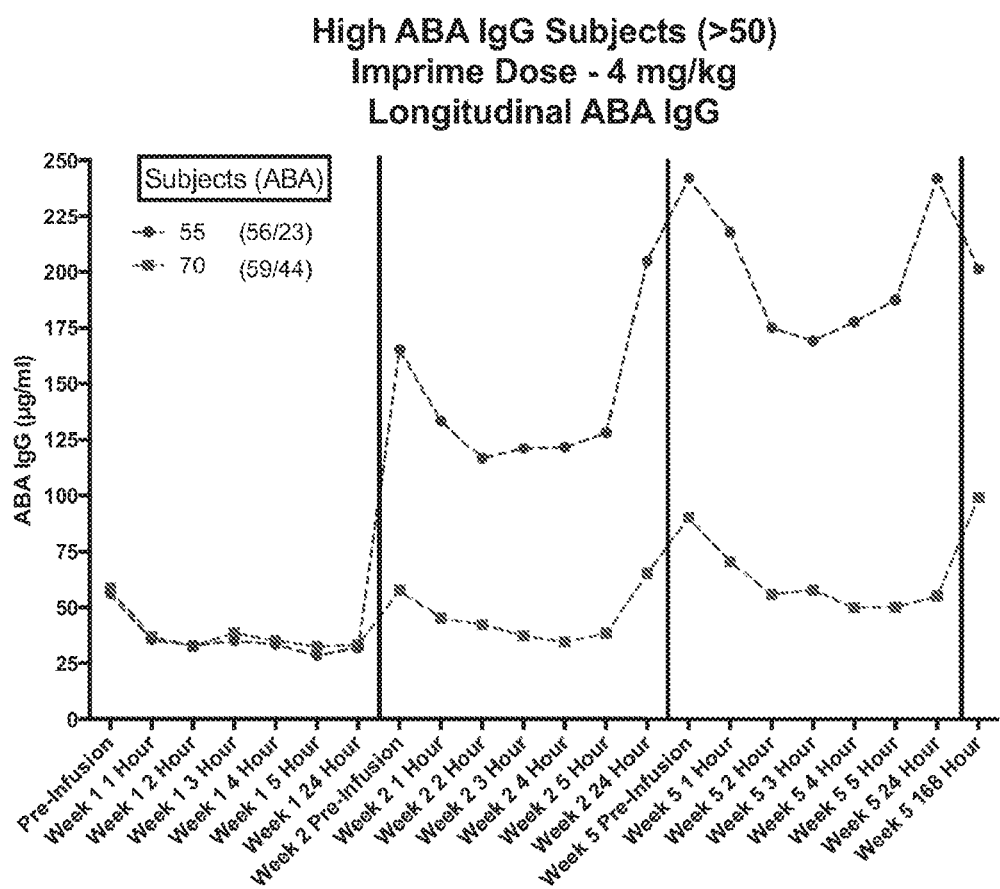
FIG. 18. Longitudinal ABA levels measured at various time points over the 5 week course of treatment in High-ABA, Mid-ABA and Low-ABA subjects.
Figure 18:
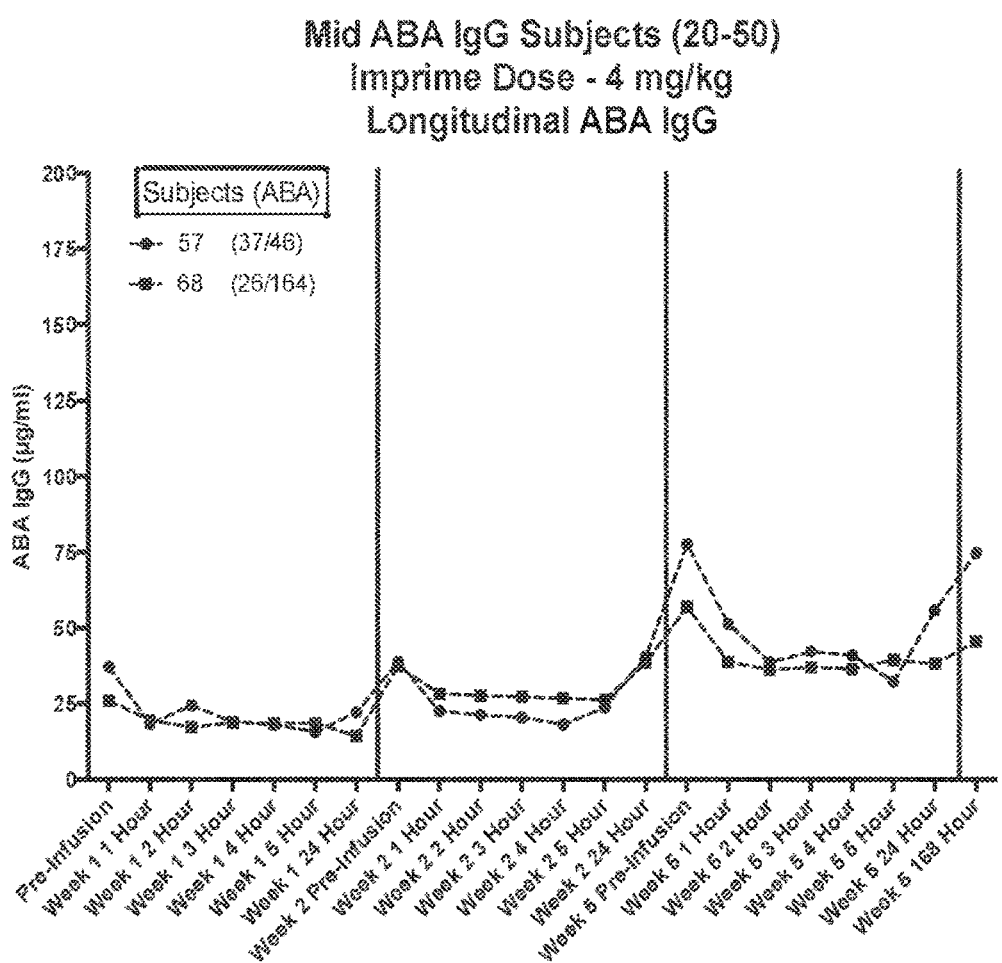
Figure 18:
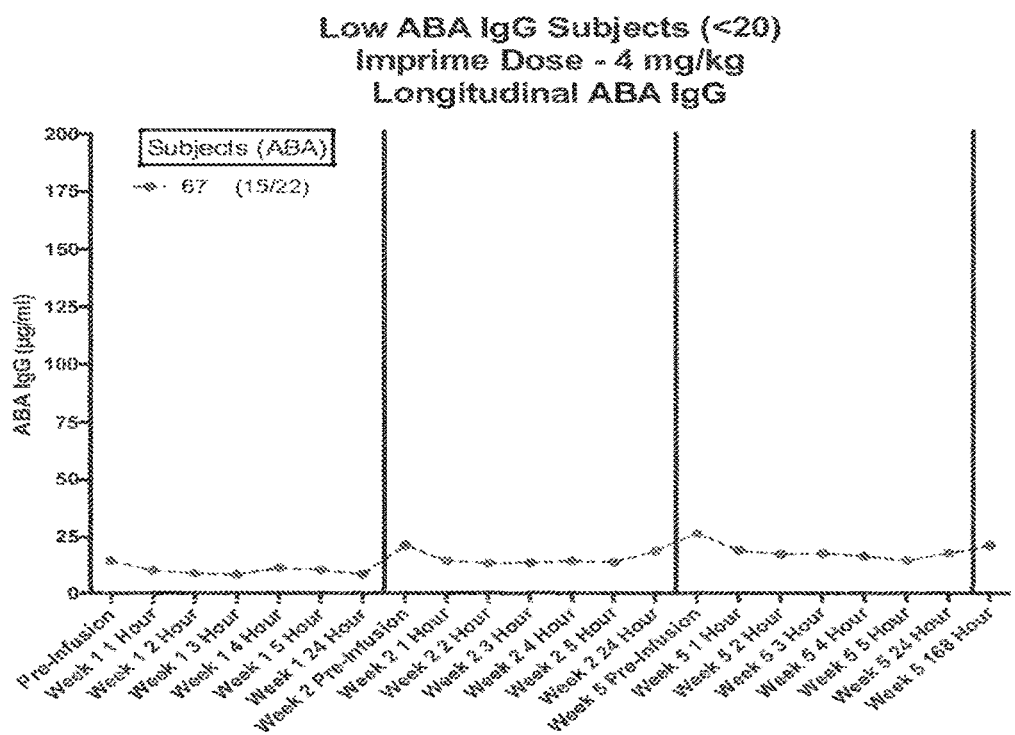

FIG. 18 shows ABA levels in High-ABA, Mid-ABA and Low-ABA subjects over the 5 week course of treatment. Increases in ABA were seen in all subjects with the largest increase occurring after administration of the week 5 dose. Significantly, the Low-ABA subject even converted to the Mid-ABA classification after the last dose.

Figure 19:
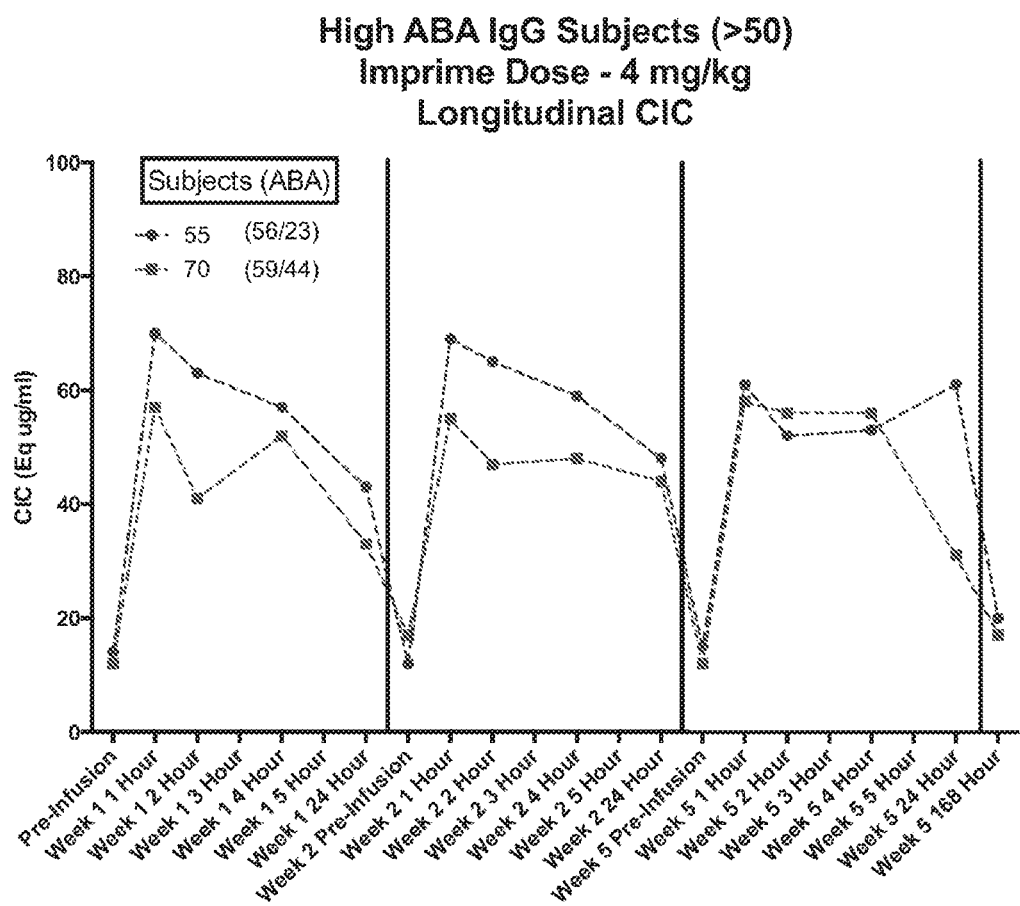
FIG. 19. Longitudinal circulating immune complex levels measured at various time points over the 5 week course of treatment in High-ABA, Mid-ABA and Low-ABA subjects.
Figure 19:
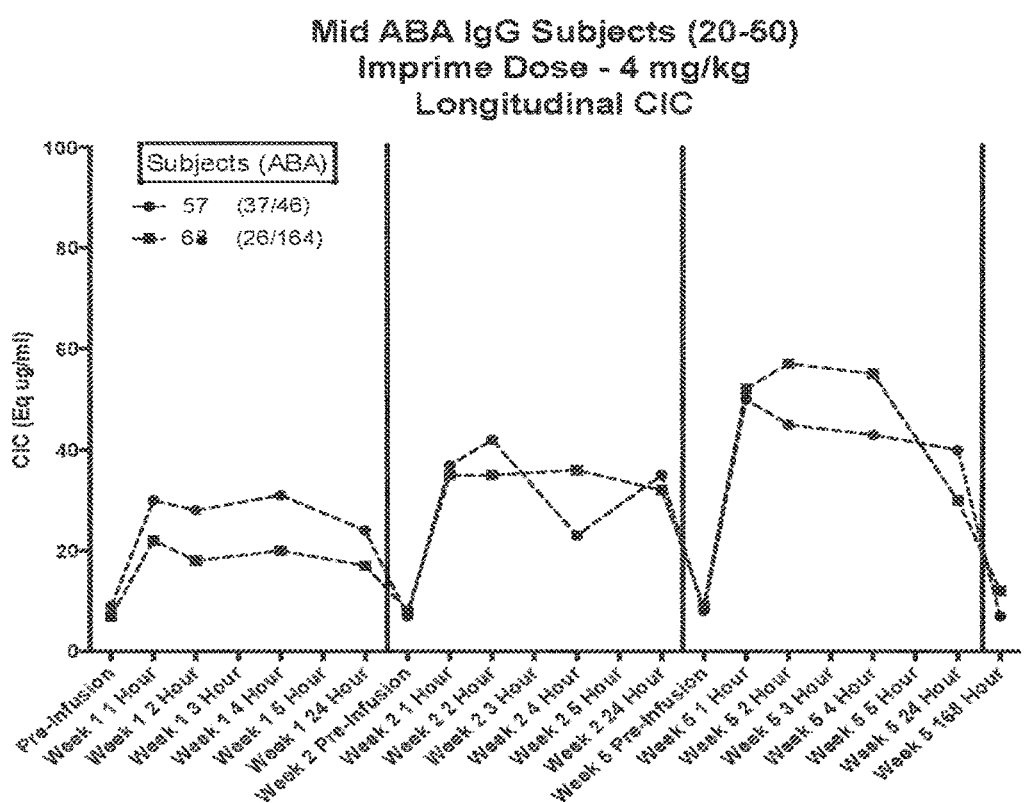
Figure 19:
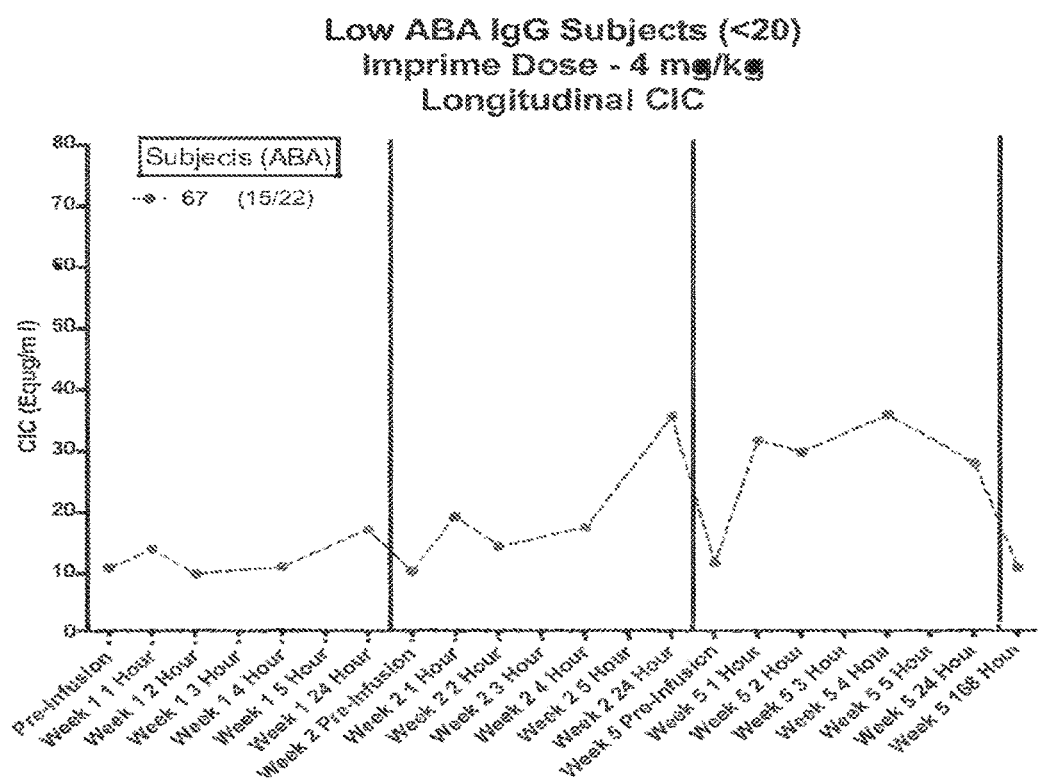
Figure 20:
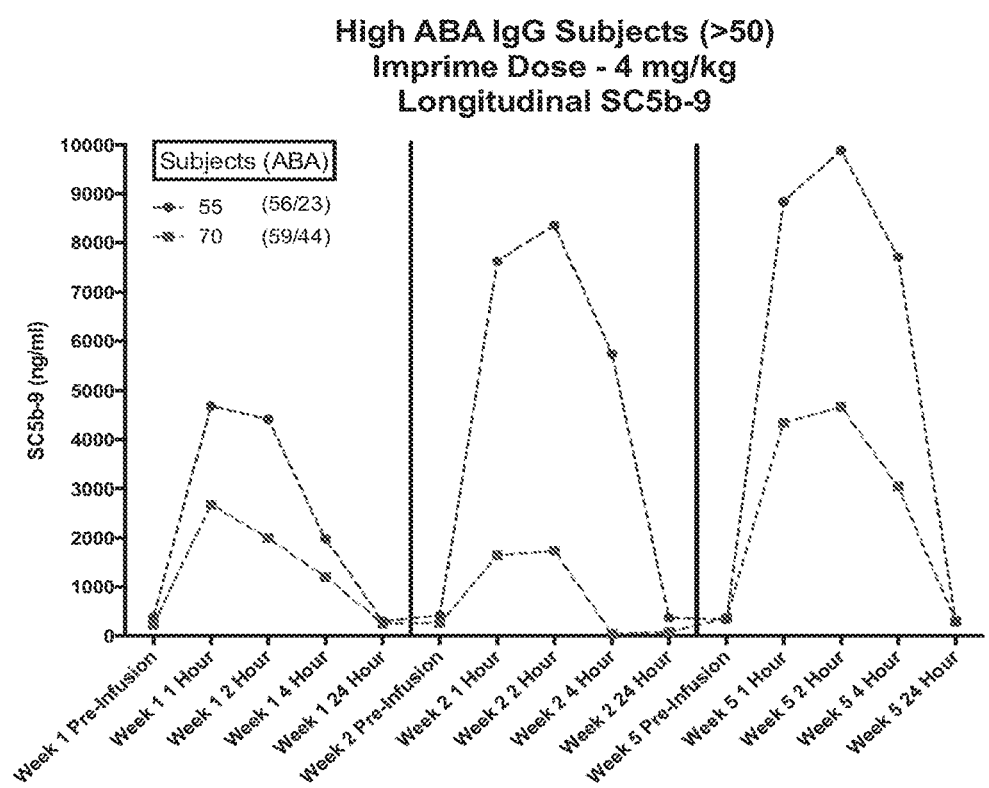
FIG. 20. Longitudinal SC5b-9 levels measured at various time points over the 5 week course of treatment in High-ABA, Mid-ABA and Low-ABA subjects.
Figure 20:
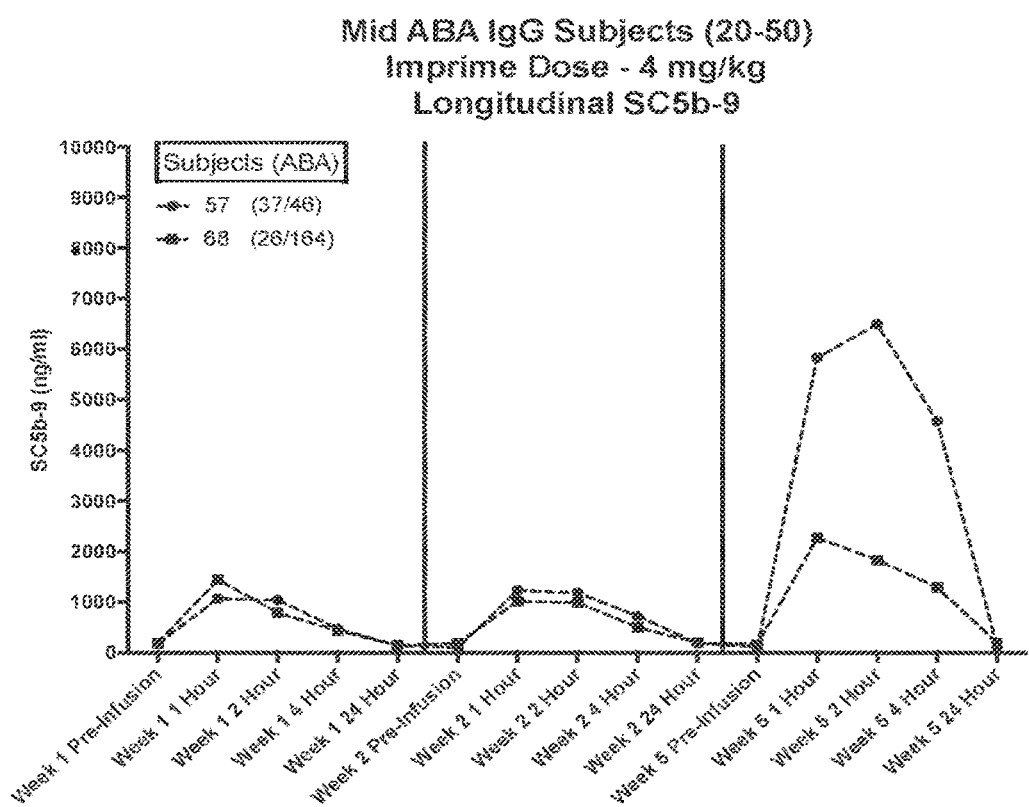
Figure 20:
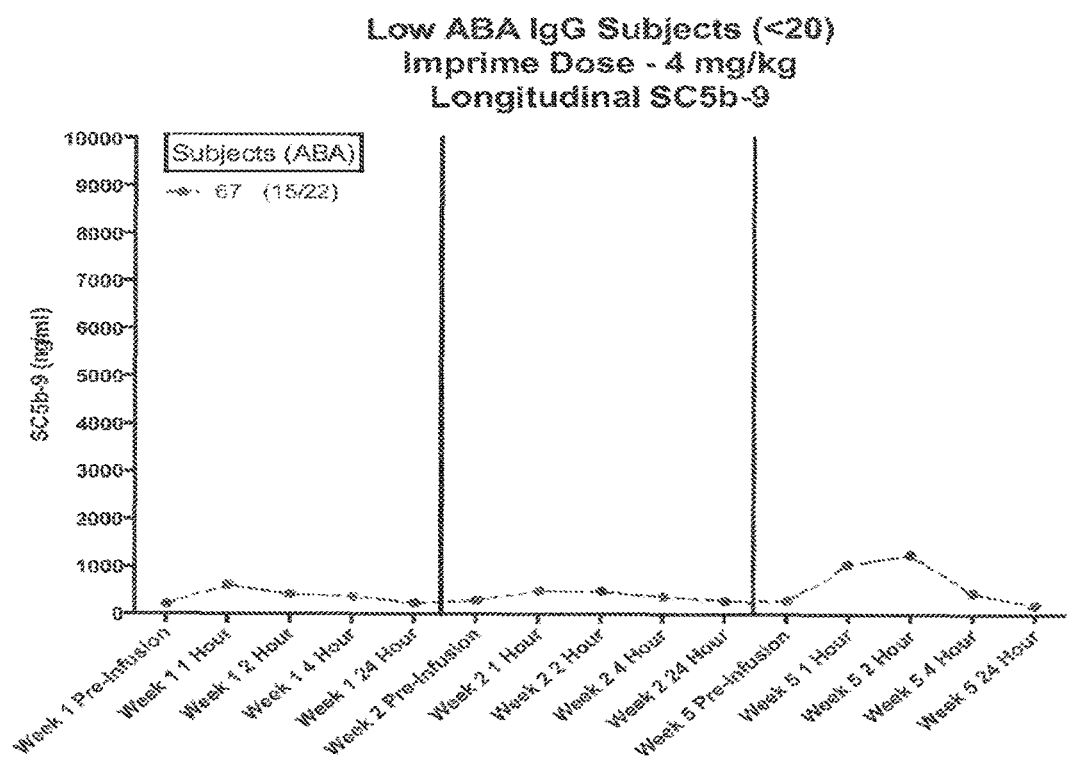
Figure 21:
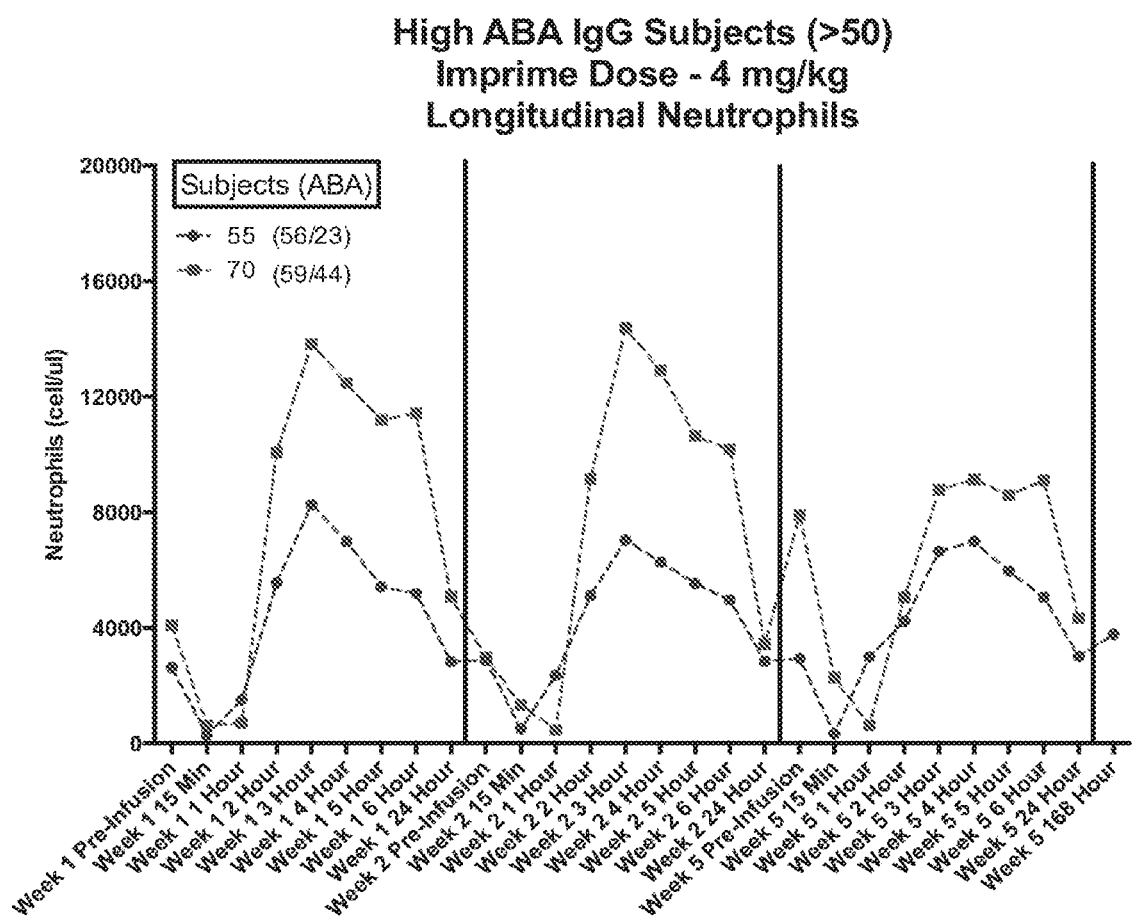
FIG. 21. Longitudinal neutrophil mobilization levels measured at various time points over the 5 week course of treatment in High-ABA, Mid-ABA and Low-ABA subjects.
Figure 21:
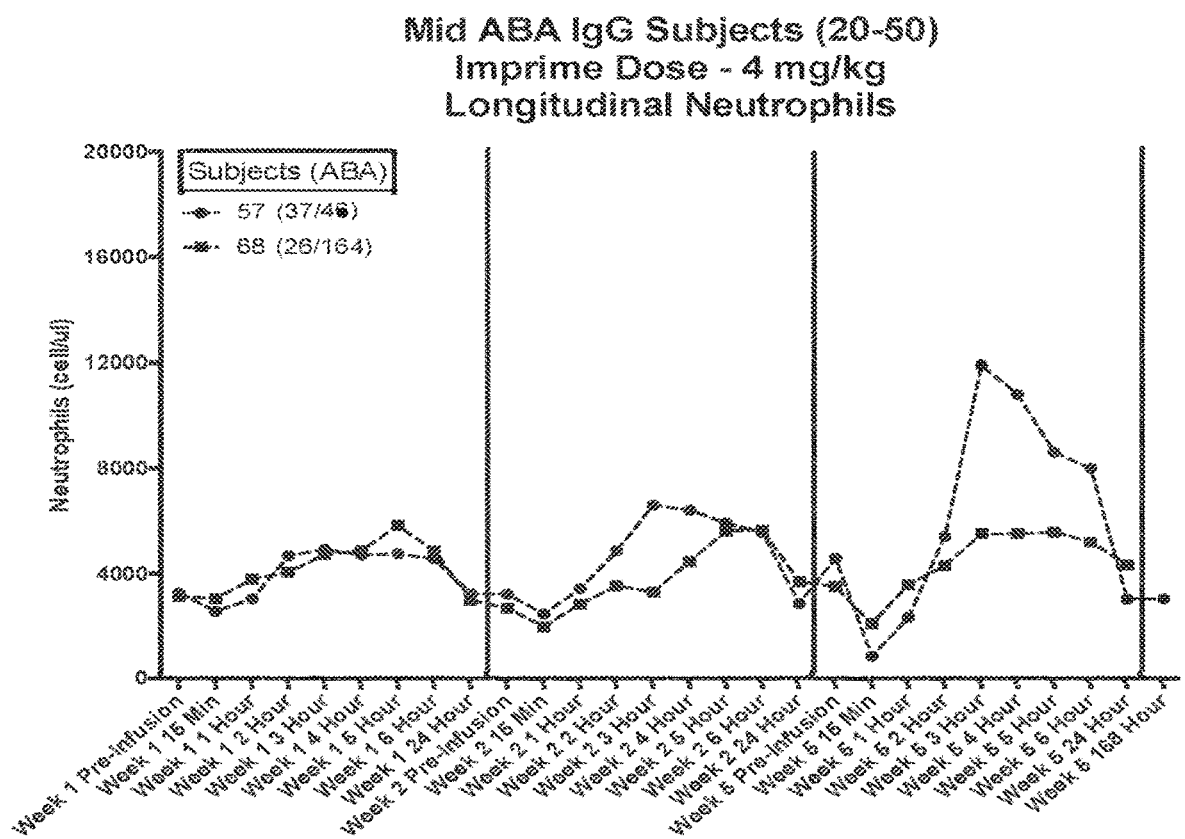
Figure 21:
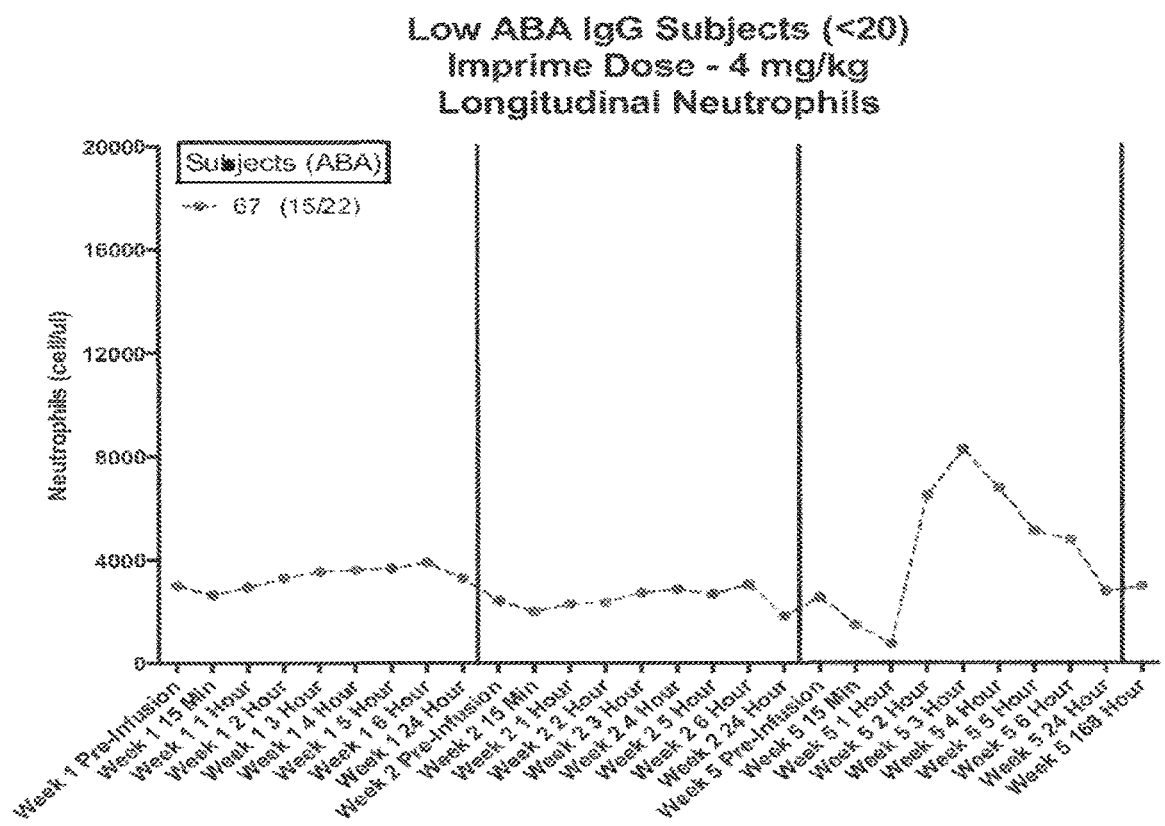
Figure 22:
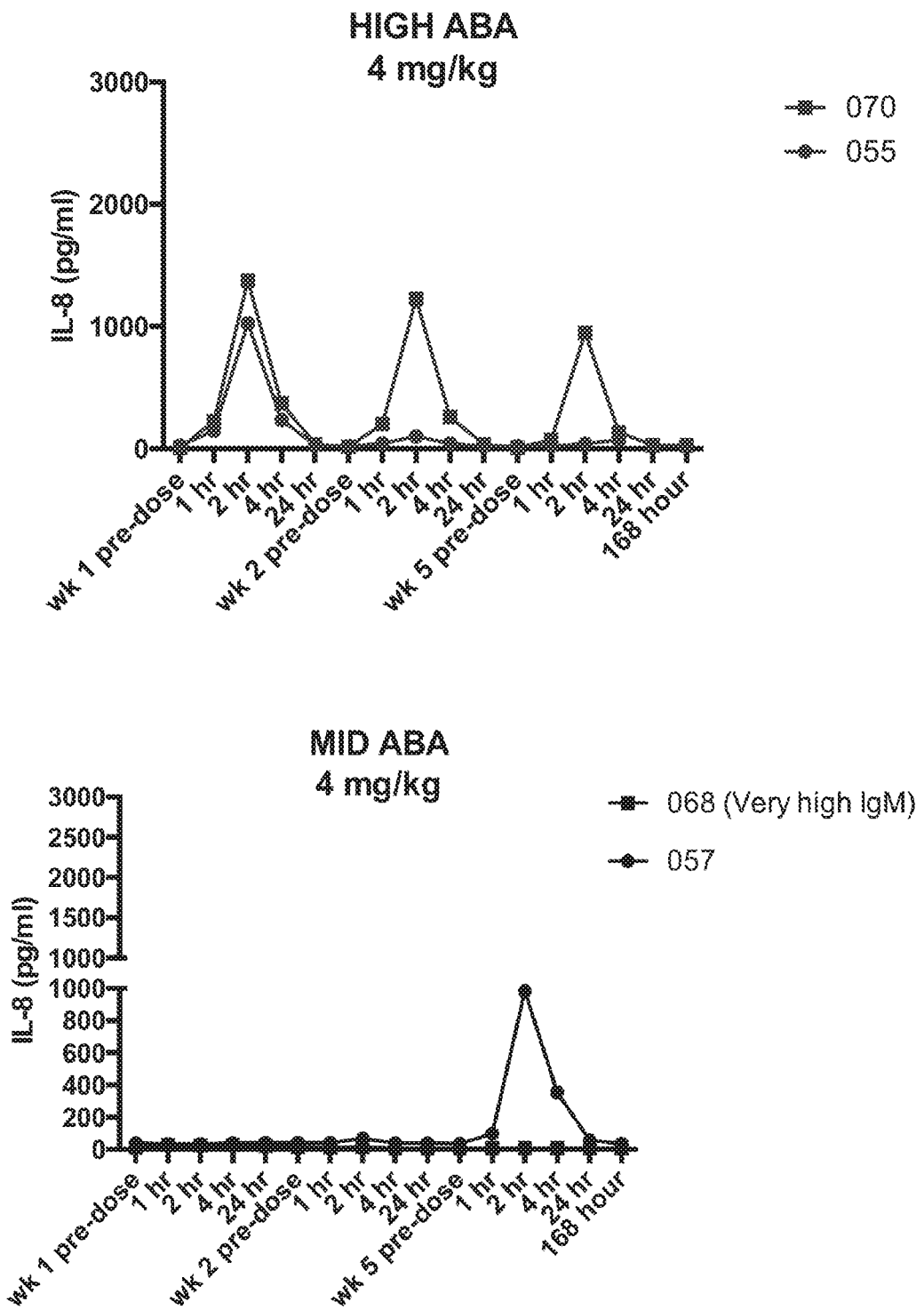
FIG. 22. Longitudinal IL-8 levels measured at various time points over the 5 week course of treatment in High-ABA, Mid-ABA and Low-ABA subjects.
Figure 22:
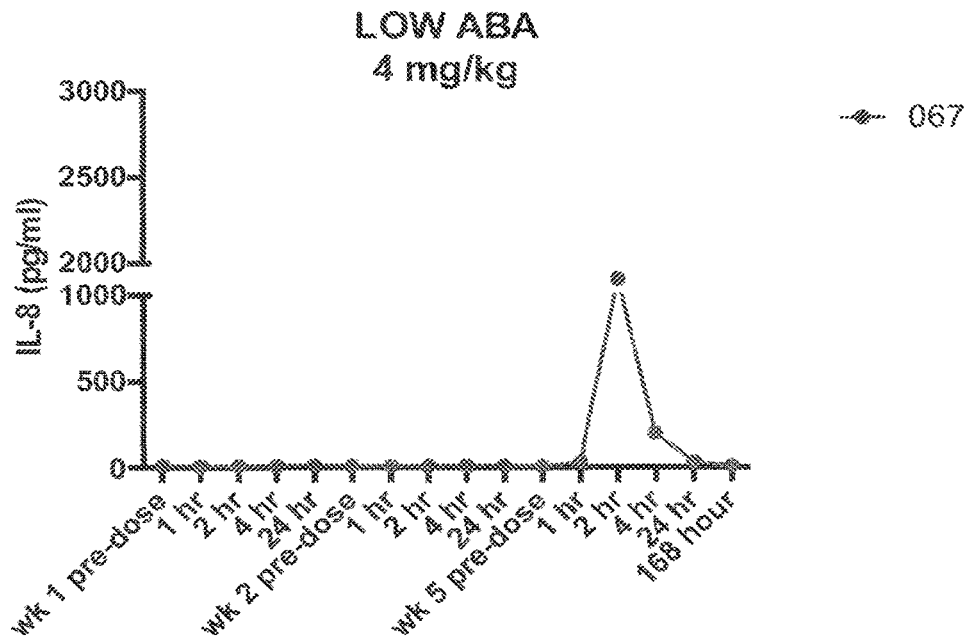
Figure 23:
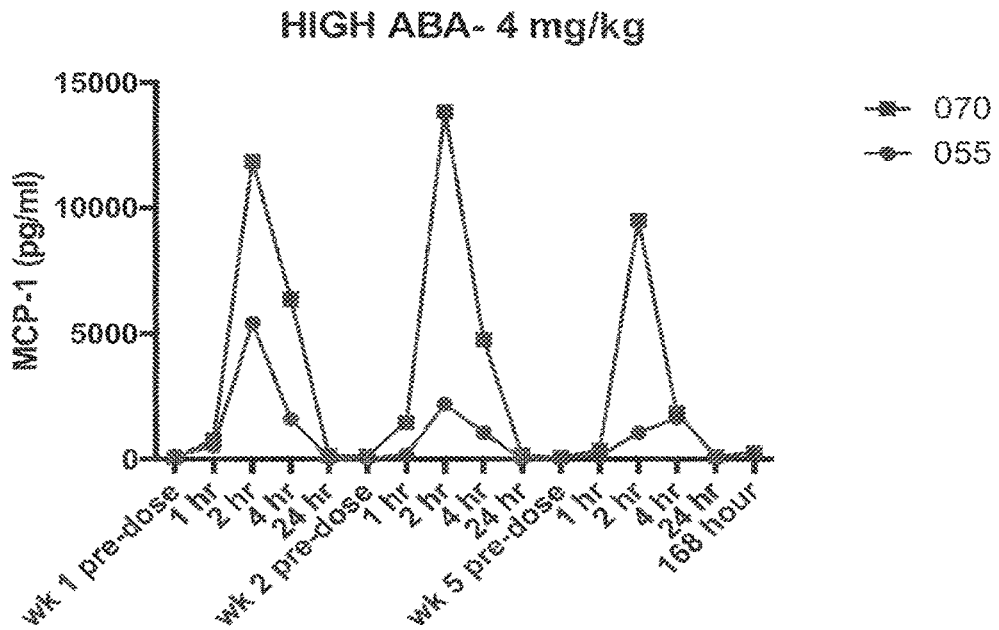
FIG. 23. Longitudinal MCP-1 levels measured at various time points over the 5 week course of treatment in High-ABA, Mid-ABA and Low-ABA subjects.
Figure 23:
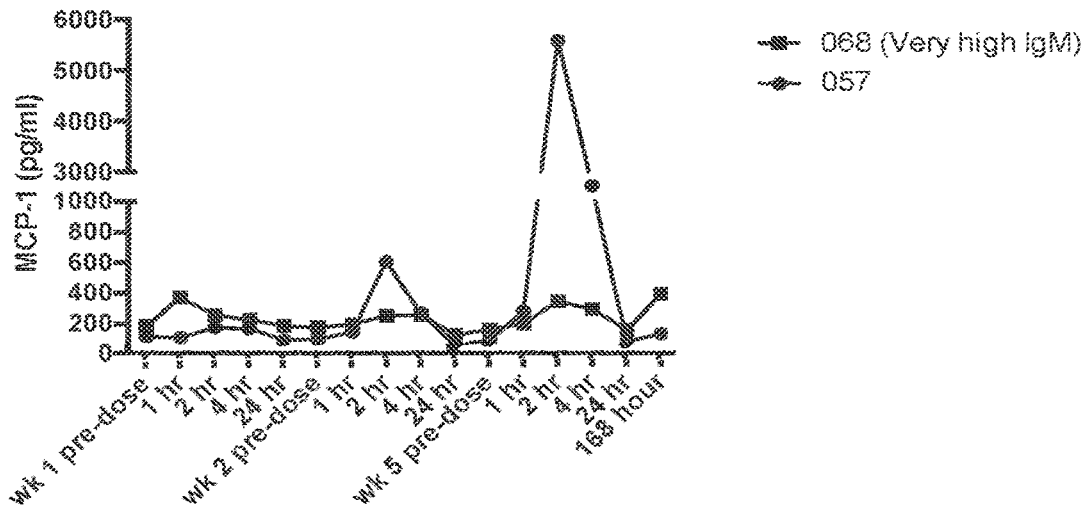
Figure 23:
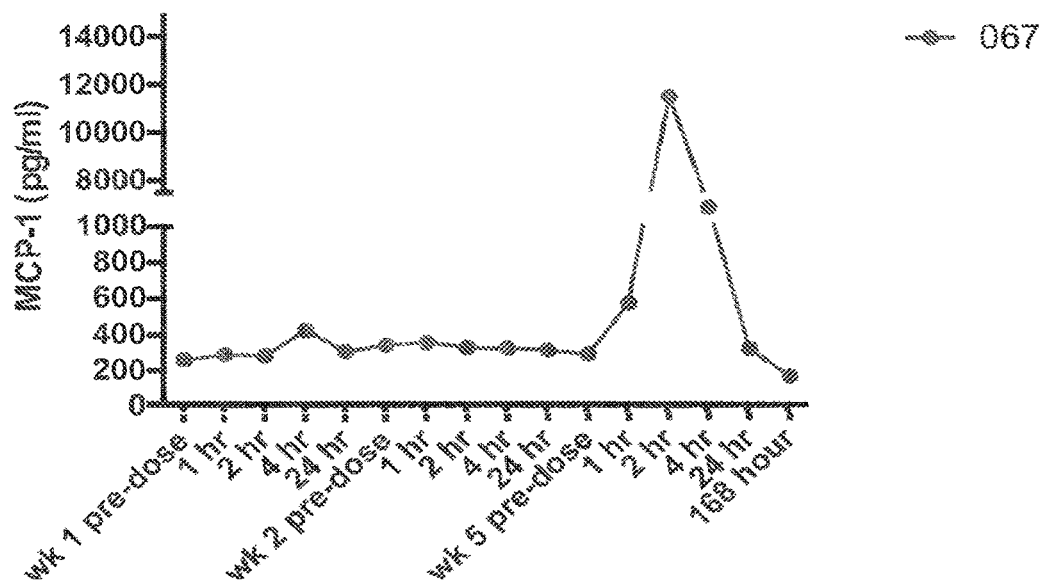

Levels of CIC (FIG. 19), SC5b-9 (FIG. 20), neutrophil mobilization (FIG. 21), IL-8 (FIG. 22) and MCP-1 (FIG. 22) were also measured over the course of treatment. As is evident from the data, acute IPD response were generated or enhanced upon dosing after a 2 week dosing interval. In some cases, acute IPD responses were only seen with the final dose—after the 2 week dosing interval. In other cases, the acute IPD responses were enhanced with the final dose. Thus, for some immunotherapies or even some individuals, increasing the amount of time between dosing with soluble β-glucan may lead to enhanced efficacy.

Increased time intervals between dosing may be, for example, every 2, 3, 4, 5, 6, 7, 8, 9, 10, 11 or 12 weeks during a course of treatment or every 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83 or 84 days. The dosing schedule will vary depending on, among other things, the type of immunotherapy, the condition being treated (cancer, infectious disease, autoimmune disease, etc.) and the subject's ABA level. In addition, the time intervals between dosing may be varied over the course of treatment.

It was also observed that the ratio of IgG ABA to IgM ABA levels may affect soluble β-glucan dosing strategies. This is particularly true for subjects in the Mid-ABA subgroup. It was found that subjects having an IgG ABA:IgM ABA ratio less than one tend to have lower IPD responses than subjects having a ratio more than one (see, for example, subject 068 in FIG. 22). Thus, subjects with a lower ratio may respond better to a higher dose of soluble β-glucan while subjects with a higher ratio may respond better to a lower dose of soluble β-glucan.

For some immunotherapies or for some individuals, it may be beneficial to have only one acute IPD response. In those cases, only one dose of soluble β-glucan would be administered.

Optimal time intervals for specific immunotherapies or specific individuals can be determined by analyzing IPD responses. These can include the IPD responses such as those described here or any others that may be relevant to certain disease conditions or immunotherapies.

Example 1

Soluble β-glucan immunotherapy was administered to a subject diagnosed with glucaganoma. The subject's ABA level prior to immunotherapy treatment placed her in the Low-ABA subgroup, and therefore, her ABA level was boosted by administration of IVIG. GAMMAGARD at 100 mg/ml was intravenously administered prior to each treatment, which provided 161 μg ABA/ml. IMPRIME PGG (Biothera Pharmaceuticals, Inc., Eagan, Minn.) at 4 mg/kg and 200 mg of pembrolizumab were separately administered intravenously on day 2 of each cycle. Each cycle was 3 weeks. Table 3 shows the subject's IgG and IgM ABA levels at various points during the treatment.

TABLE 3

| Sample | ABA IgG (μg/ml) | ABA IgM (μg/ml) |
|---|---|---|
| cycle 1, day 1 pre-IVIG | 1.0 | 9.6 |
| cycle 1, day 1 post-IVIG | 49.9 | 9.1 |
| cycle 1, day 2 pre-IMPRIME | 33.2 | 9.4 |
| cycle 1, day 2 EOI IMPRIME | 17.9 | 6.0 |
| cycle 1, day 2 EOI pembro | 18.2 | 5.3 |
| cycle 1, day 3 | 14.5 | 8.3 |
| cycle 1, day 9 | 10.2 | 10.1 |
| cycle 2, day 1 pre-IVIG | 22.3 | 18.5 |
| cycle 2, day 1 post-IVIG | 83.9 | 15.7 |
| cycle 2, day 1 EOI-IMPRIME | 50.4 | 11.7 |
| cycle 2, day 1 EOI-pembro | 49.4 | 9.6 |
| cycle 3, day 1 pre-IVIG | 21.9 | — |
| cycle 3, day 1 post-IVIG | 78.7 | — |
| cycle 3, day 1 EOI-IMPRIME | 57.4 | — |
| cycle 3, day 1 EOI-pembro | 60.7 | — |

The addition of IVIG converted the status of the subject from Low-ABA to High-ABA and, by cycle 3, the subject remained in the High-ABA subgroup even prior to administration of IVIG.

Figure 24:
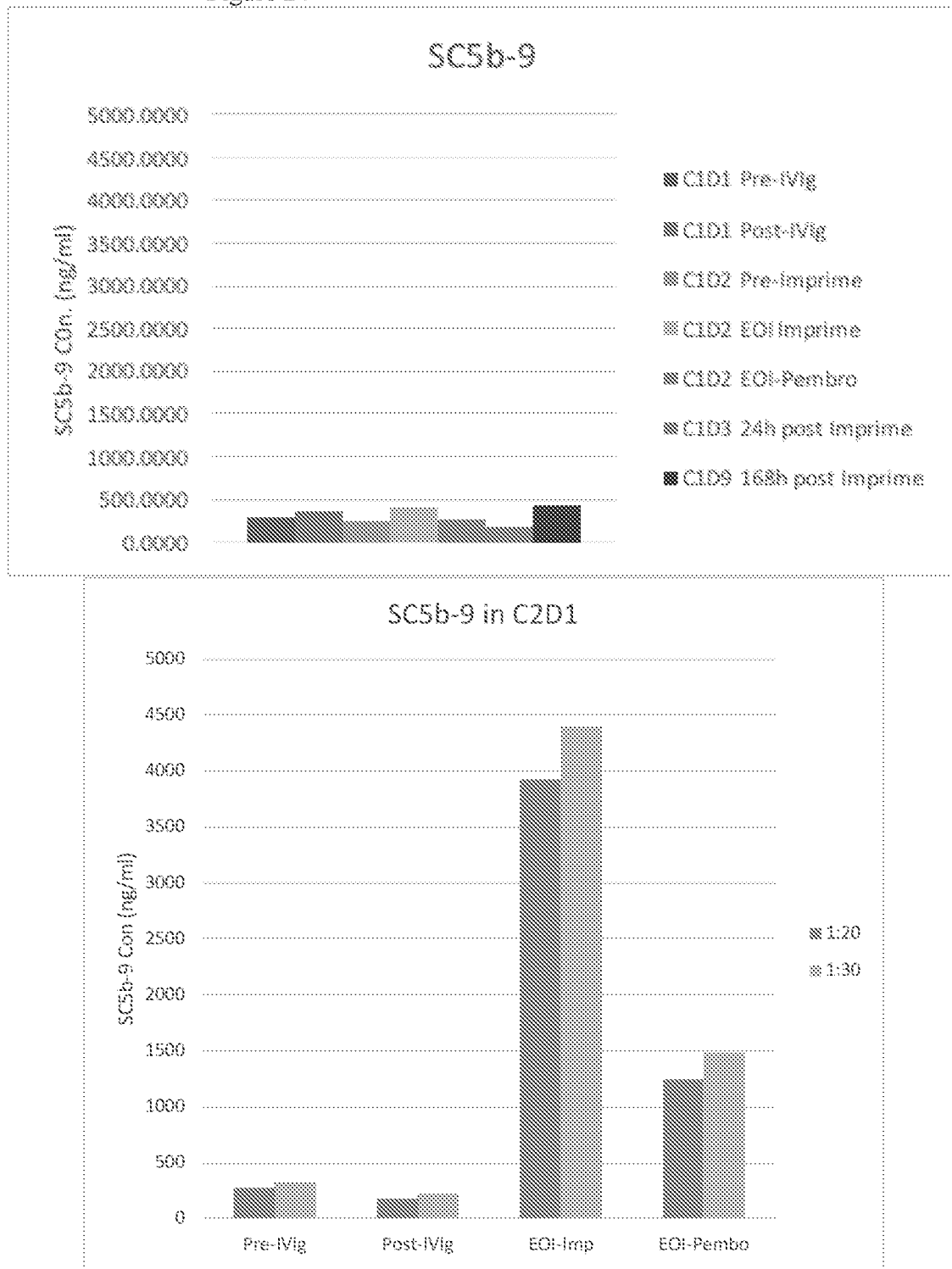
FIG. 24. SC5b-9 levels measured at various time points in a cancer subject receiving soluble β-glucan immunotherapy, which is administered once every 3 weeks.
Figure 24:
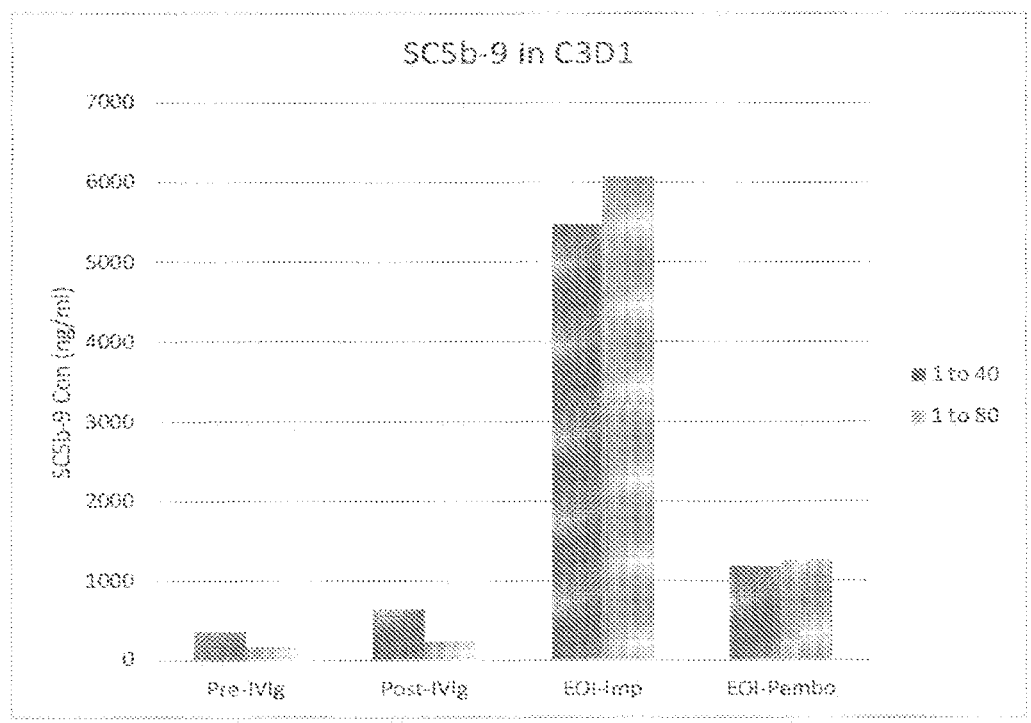
Figure 25:
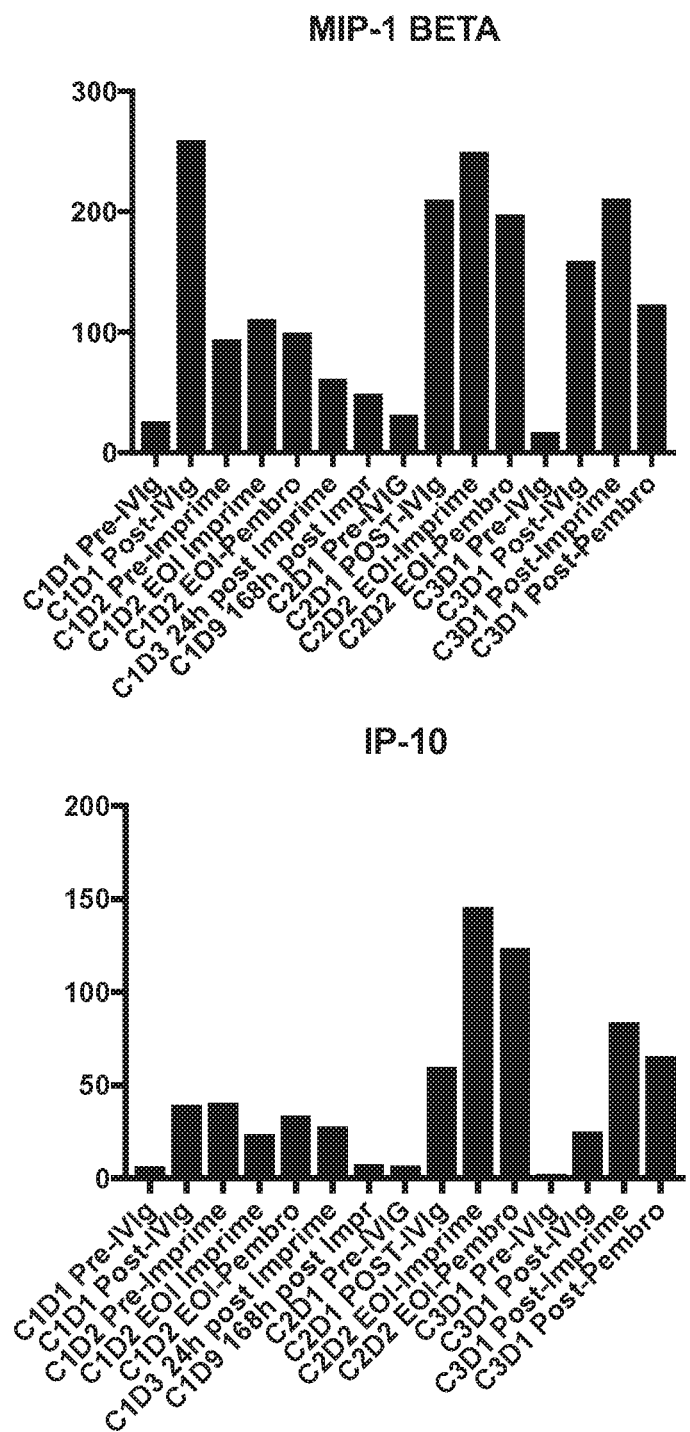
FIG. 25 MIP-1β and IP-10 levels measured at various time points in a cancer subject receiving soluble β-glucan immunotherapy, which is administered once every 3 weeks.
Figure 26:
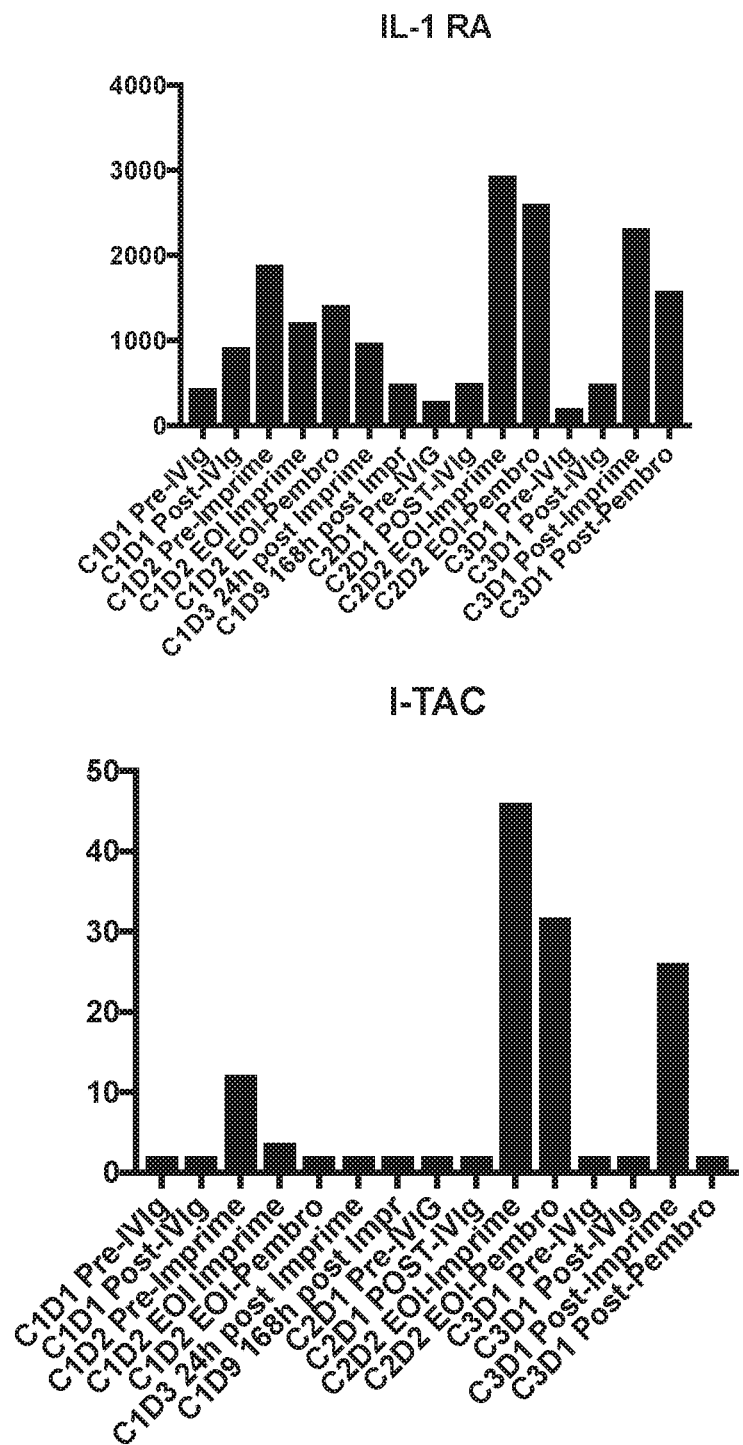
FIG. 26. IL-1 RA and I-TAC levels measured at various time points in a cancer subject receiving soluble β-glucan immunotherapy, which is administered once every 3 weeks.

Complement activation was assessed by measuring levels of SC5b-9 at various time points and the results are shown in FIG. 24. Acute increases in complement activation corresponded with the subject's conversion to the High-ABA subgroup. Cytokine levels were also measured during the immunotherapy treatment. MIP-1b, IP-10, IL-1 RA and I-TAC were evaluated and the results are shown in FIGS. 25 and 26. Again, acute IPD responses were seen with conversion to the High-ABA group. Importantly, when soluble β-glucan was administered once every 3 weeks, these robust, acute IPD responses occurred with each administration. The IPD responses did not decrease and level off, which indicates that the immunotherapy will remain effective and may even be more effective than, for example, weekly dosing. In addition, less frequent dosing is more convenient and economical for the subject.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shah govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:
1. A method comprising:
   obtaining a biological sample from a subject in need of β-glucan immunotherapy;
   analyzing the biological sample for a biomarker anti-β-glucan antibody (ABA) level;
   classifying the subject into a subgroup selected from the group consisting of low-level ABA subjects, mid-level ABA subjects, and high-level ABA subjects based on the biomarker ABA level, wherein low-level ABA subjects have an ABA level of less than 20 μg/mL, mid-level ABA subjects have an ABA level between 20

μg/mL and 50 μg/mL, and high-level ABA subjects have an ABA level of greater than 50 μg/mL;

identifying an appropriate dose strategy of soluble β-glucan for the subject based on the subject's subgroup, wherein the appropriate dose strategy for the low-level ABA subgroup and the mid-level ABA subgroup comprises administering one or more doses of soluble β-glucan of at least 4 mg/kg to the subject and the appropriate dose strategy for the high-level ABA subgroup comprises administering one or more doses of soluble R-glucan of about 2 mg/kg to the subject; and administering the soluble β-glucan to the subject according to the appropriate dose strategy.

2. The method of claim 1, wherein the biomarker ABA comprises IgG.

3. The method of claim 1, wherein the appropriate dose strategy comprises pre-dosing the subject in need of β-glucan immunotherapy based on the subject's subgroup 1 or more times with soluble β-glucan.

4. The method of claim 1, wherein the soluble β-glucan is derived from yeast.

5. The method of claim 1, wherein the soluble β-glucan comprises a β-1,3/1,6 glucan.

6. The method of claim 1, wherein the soluble β-glucan comprises β(1,6)-[poly-(1,3)-D-glucopyranosyl]-poly-β(1,3)-D-glucopyranose.

7. The method of claim 1, wherein the at least 4 mg/kg dose of soluble β-glucan is administered to the subject weekly.

* * * * *